United States Patent
Kawakami et al.

(10) Patent No.: US 10,456,171 B2
(45) Date of Patent: Oct. 29, 2019

(54) SPINAL CORRECTION SYSTEM AND METHOD

(71) Applicant: WARSAW ORTHOPEDIC, INC., Warsaw, IN (US)

(72) Inventors: Noriaki Kawakami, Aichi prefecture (JP); Geoffrey Askin, Newstead (AU); Haemish Crawford, Remuera Auckland (NZ); Roy Lim, Germantown, TN (US); Adam D. Glaser, Germantown, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 89 days.

(21) Appl. No.: 15/225,078

(22) Filed: Aug. 1, 2016

(65) Prior Publication Data
US 2016/0338740 A1    Nov. 24, 2016

Related U.S. Application Data

(62) Division of application No. 13/495,079, filed on Jun. 13, 2012, now Pat. No. 9,427,261.

(51) Int. Cl.
*A61B 17/70* (2006.01)
*A61B 17/88* (2006.01)

(52) U.S. Cl.
CPC ........ *A61B 17/7014* (2013.01); *A61B 17/707* (2013.01); *A61B 17/888* (2013.01)

(58) Field of Classification Search
CPC ....... A61B 17/60; A61B 17/66; A61B 17/663; A61B 17/666; A61B 17/7013; A61B 17/7014; A61B 17/7016; A61B 17/7017; A61B 17/7019; A61B 17/72; A61B 17/7216; A61B 17/7233; A61B 17/8004; A61B 17/8009; A61B 17/8023
See application file for complete search history.

(56) References Cited

U.S. PATENT DOCUMENTS

| 5,516,335 | A  | * | 5/1996  | Kummer  | A61B 17/7216 606/63 |
| 7,942,908 | B2 |   | 5/2011  | Sacher et al. | |
| 7,955,357 | B2 |   | 6/2011  | Kiester | |
| 8,568,457 | B2 | * | 10/2013 | Hunziker | A61B 17/7016 606/246 |
| 8,658,457 | B2 | * | 2/2014  | Miyoshi | H01L 27/1463 257/E27.152 |
| 9,060,810 | B2 | * | 6/2015  | Kercher | A61B 17/7011 |
| 2004/0153067 | A1 |  | 8/2004  | Smith et al. | |

(Continued)

FOREIGN PATENT DOCUMENTS

WO    2012044371 A1    4/2012

OTHER PUBLICATIONS

Supplementary European Search Report of the European Patent Office, dated Mar. 15, 2016, of European Patent Application No. 13804883.0 filed May 31, 2013.

*Primary Examiner* — Lynnsy M Summitt

(57) ABSTRACT

A spinal correction apparatus comprises a body. A ratchet is disposed with the body. A longitudinal element is connected to the ratchet. A force is applied to at least a portion of the apparatus that causes dynamic incremental movement of the longitudinal element relative to the body in at least one direction. Methods of use are disclosed.

18 Claims, 24 Drawing Sheets

(56) References Cited

U.S. PATENT DOCUMENTS

| | | | |
|---|---|---|---|
| 2006/0195088 A1* | 8/2006 | Sacher | A61B 17/7014 606/279 |
| 2008/0195100 A1* | 8/2008 | Capote | A61B 17/7091 606/71 |
| 2009/0306717 A1* | 12/2009 | Kercher | A61B 17/7011 606/258 |
| 2010/0004697 A1* | 1/2010 | Fortin | A61B 17/66 606/86 R |
| 2011/0137347 A1* | 6/2011 | Hunziker | A61B 17/7016 606/258 |
| 2013/0296857 A1* | 11/2013 | Barnett | A61B 17/6416 606/57 |

* cited by examiner

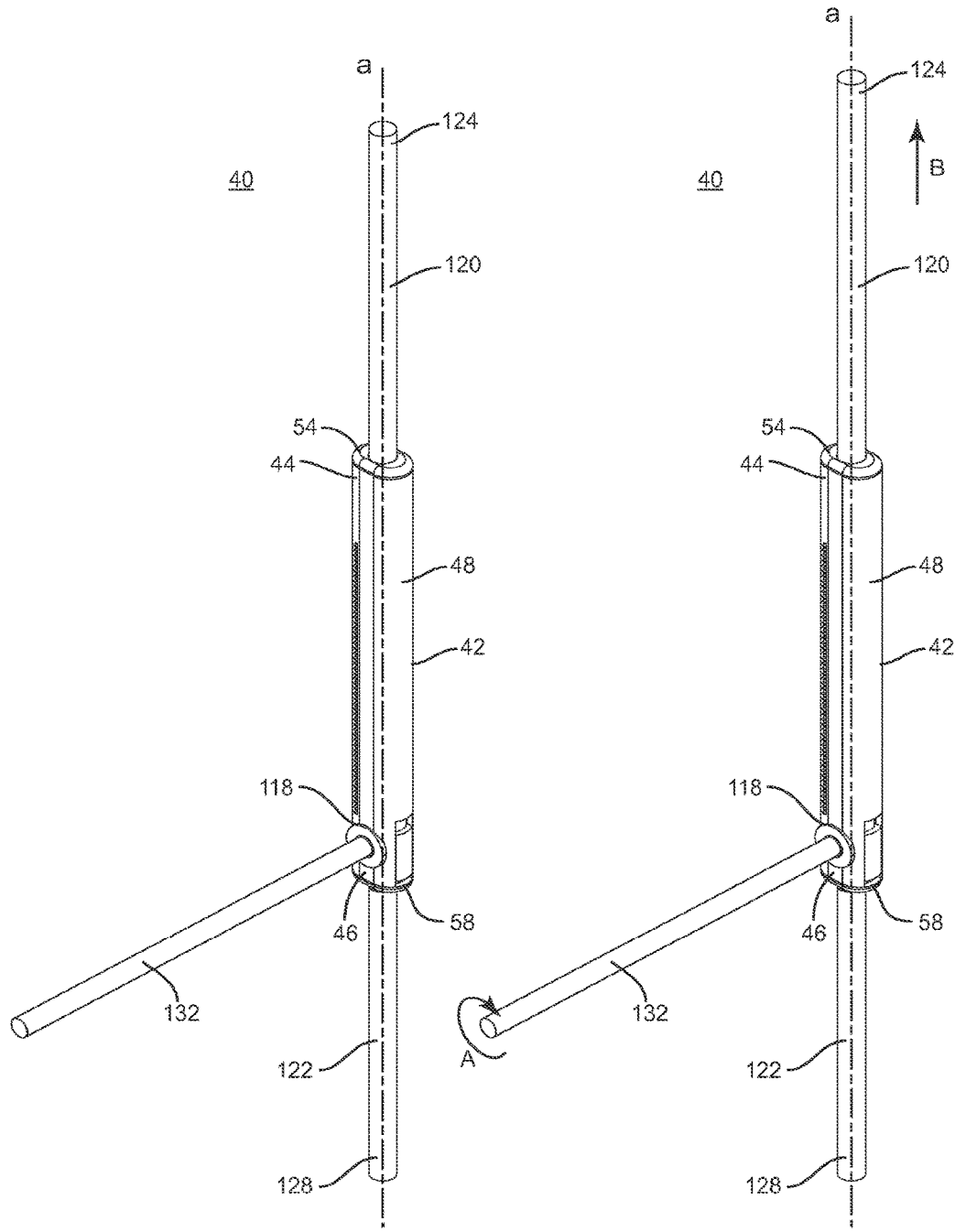

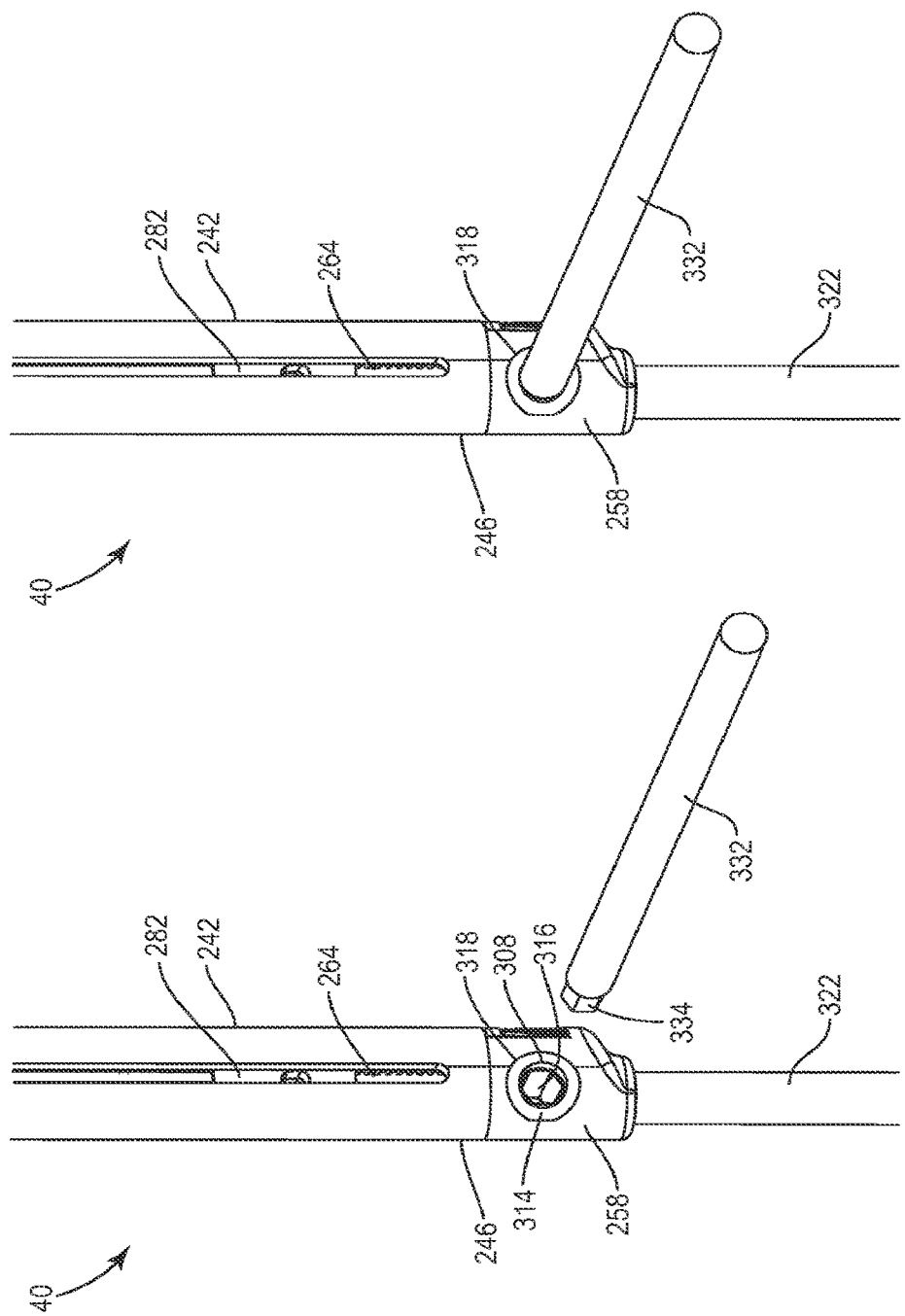

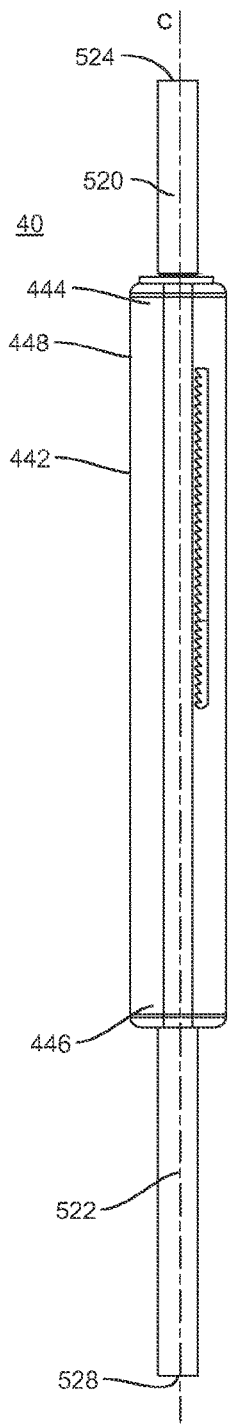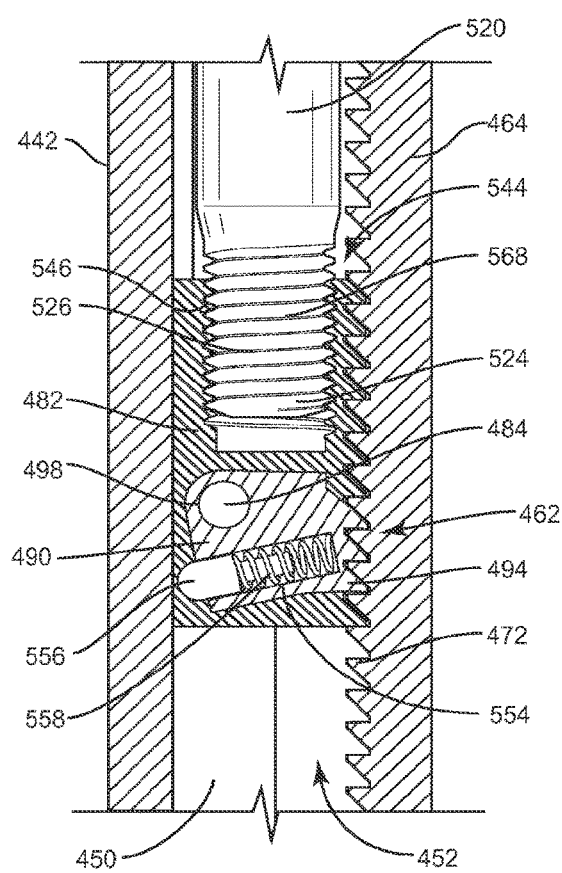
FIG. 30
FIG. 31

SPINAL CORRECTION SYSTEM AND METHOD

CROSS REFERENCE TO RELATED APPLICATIONS

This application is a divisional application of U.S. patent application Ser. No. 13/495,079, filed Jun. 13, 2012, which is incorporated by reference herein, in its entirety.

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as rods or tethers, for stabilization of a treated section of a spine. This disclosure describes an improvement over these prior art technologies.

SUMMARY

Accordingly, a surgical system and method are provided. In one embodiment, in accordance with the principles of the present disclosure, a spinal correction apparatus is provided. The spinal correction apparatus comprises a body. A ratchet is disposed with the body. A longitudinal element is connected to the ratchet. A force is applied to at least a portion of the apparatus that causes dynamic incremental movement of the longitudinal element relative to the body in at least one direction.

In one embodiment, the spinal correction apparatus comprises an outer sleeve extending between a first end and a second end. The outer sleeve includes an inner surface that defines an elongated cavity. A ratchet is disposed with the cavity of the outer sleeve. The ratchet comprises an inner sleeve including a first rack and a second rack formed on the inner surface of the outer sleeve. The ratchet further comprises a carriage, a first pawl engageable with the first rack and a second pawl engageable with the second rack. A rod is telescopically oriented with the outer sleeve and connected to the carriage. The rod extends between a first end and a second end. A rotatable cam is engageable with the inner sleeve in a configuration to facilitate incremental movement of the rod relative to the outer sleeve in a first axial direction. The cam defines a socket configured for engagement with an instrument. An expansion force is applied to the first end of the rod, which causes incremental movement of the rod, independent of the cam, relative to the outer sleeve in the first axial direction.

In one embodiment, the spinal correction apparatus comprises an outer sleeve extending between a first end and a second end. The outer sleeve includes an inner surface that defines an elongated cavity. A ratchet is disposed with the cavity of the outer sleeve. The ratchet comprises a drive screw, a carriage and a helical pawl being engageable with the carriage. A rod is telescopically oriented with the outer sleeve and connected to the carriage. The rod extends between a first end and a second end. A worm gear is engageable with the screw in a configuration to facilitate incremental movement of the rod relative to the outer sleeve in a first axial direction and a second axial direction. The worm gear defines a socket configured for engagement with an instrument. An expansion force is applied to the first end of the rod, which causes incremental movement of the rod, independent of the worm gear, relative to the outer sleeve in the first axial direction.

BRIEF DESCRIPTION OF THE DRAWINGS

The present disclosure will become more readily apparent from the specific description accompanied by the following drawings, in which:

FIG. 6 is a perspective view of the system and tool shown in FIG. 5;

FIG. 7 is a perspective view of the system and tool shown in FIG. 5;

FIG. 19 is a perspective break away view of the system shown in FIG. 16 including a tool;

FIG. 20 is a perspective break away view of the system and tool shown in FIG. 19;

FIG. 30 is a perspective view of one particular embodiment of a system including a spinal correction apparatus in accordance with the principles of the present disclosure;

FIG. 31 is a cross sectional break away view of the system shown in FIG. 30;

Like reference numerals indicate similar parts throughout the figures.

DETAILED DESCRIPTION

Figure 1:
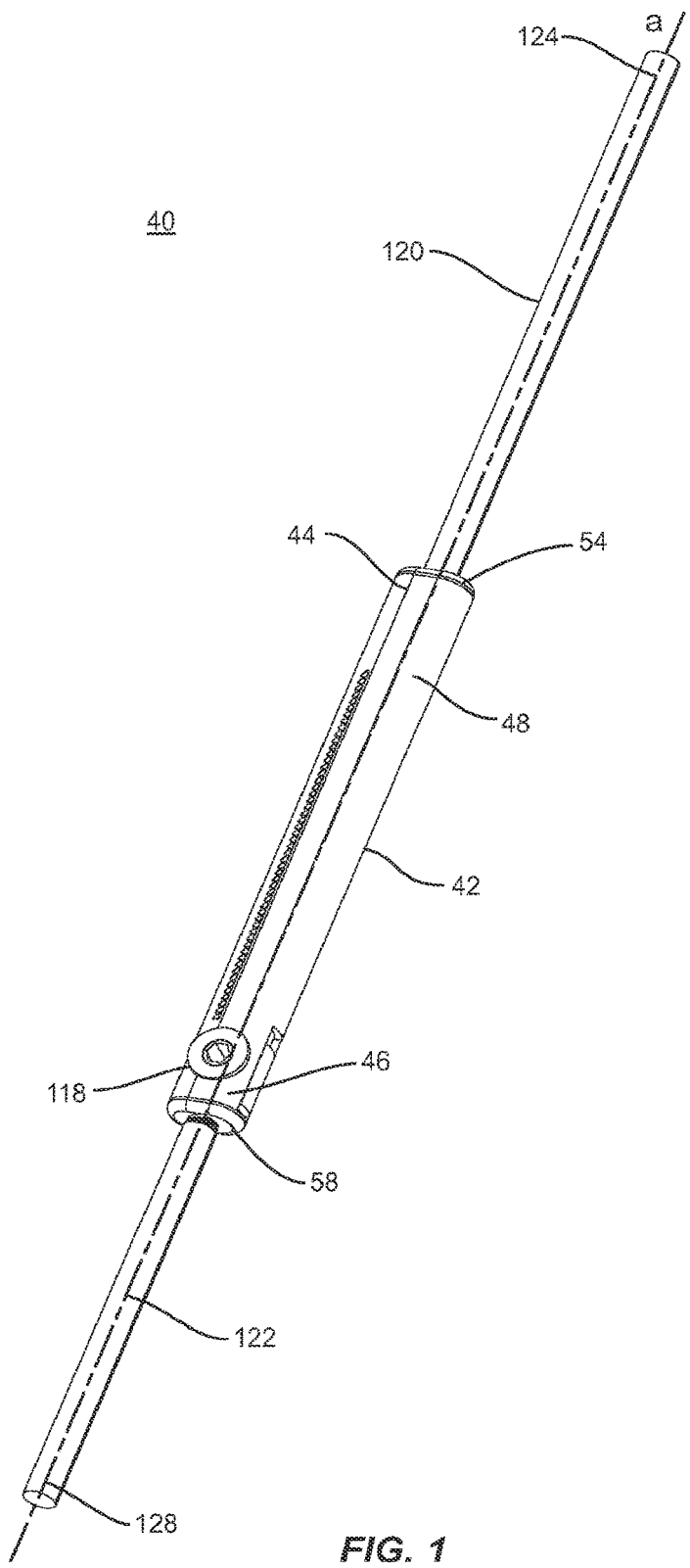
FIG. 1 is a perspective view of one particular embodiment of a system including a spinal correction apparatus in accordance with the principles of the present disclosure.
Figure 2:
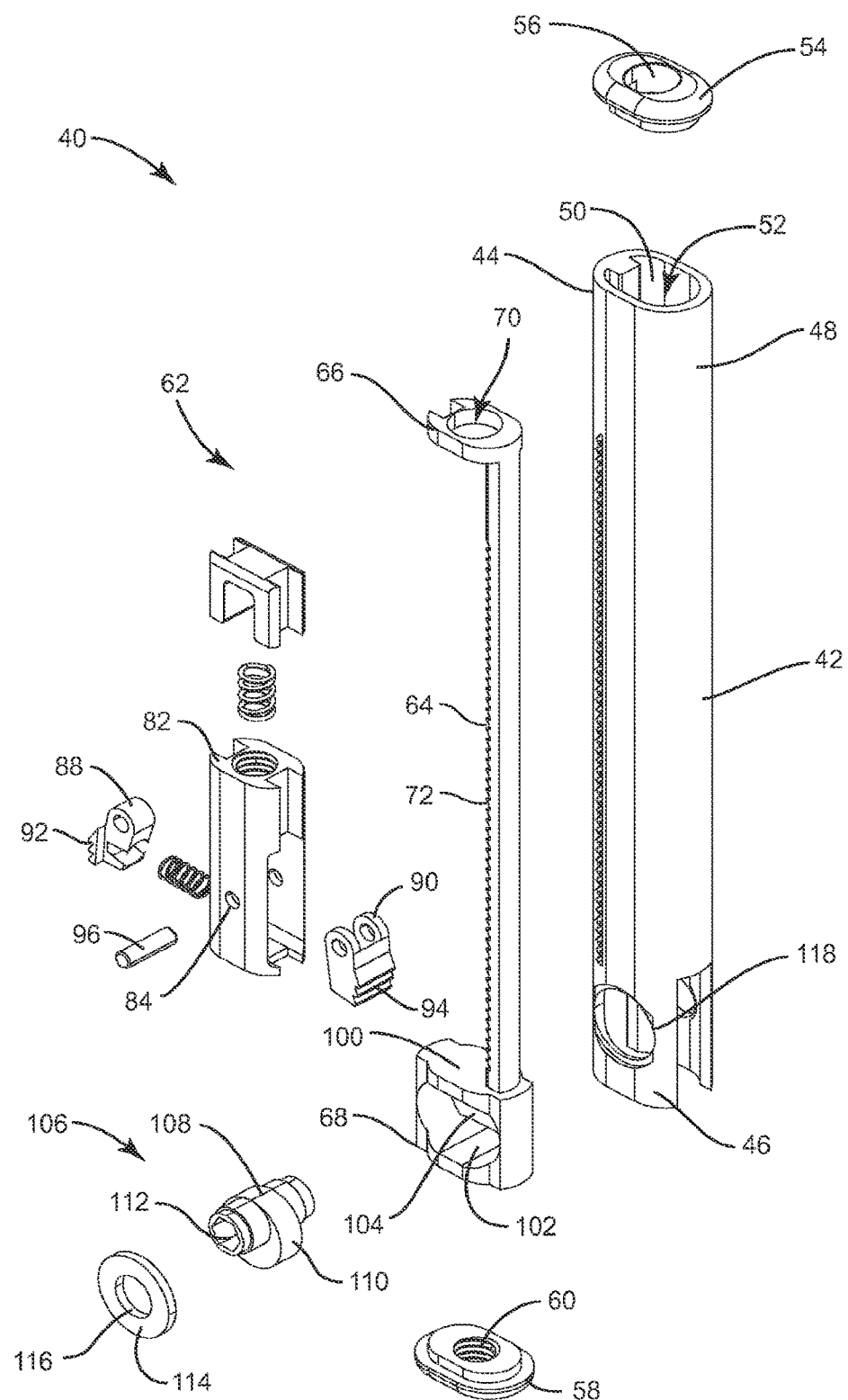
FIG. 2 is a perspective view of the components of the system shown in FIG. 1 with parts separated.
Figure 3:
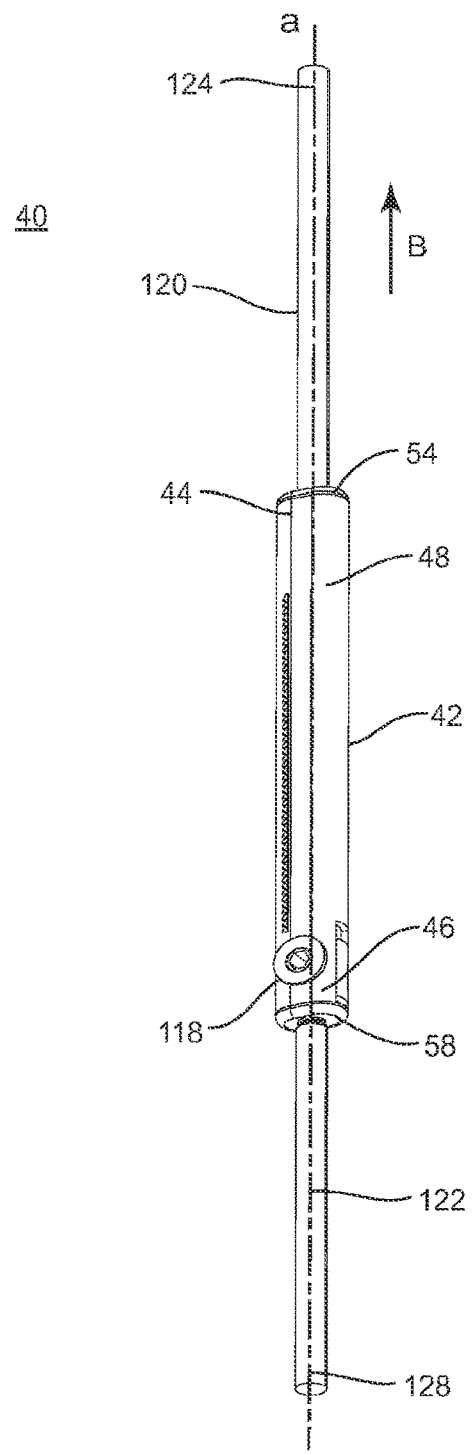
FIG. 3 is a perspective view of the system shown in FIG. 1.

The exemplary embodiments of the surgical system and related methods of use of the present disclosure are discussed in terms of medical devices for the treatment of musculoskeletal disorders and more particularly, in terms of a spinal correction apparatus. It is envisioned that the spinal correction apparatus may be employed in applications for correction of deformities, such as, for example, kyphosis and scoliosis.

In one embodiment, the system includes a spinal correction apparatus that provides a ratcheting extension with a back-up drive extension. The system may comprise a minimal metal on metal design. The components of the system may comprise about a 4.5 inch (in) rod with about a 50 millimeter (mm) extension or about a 5.5 in rod with about a 100 mm extension. The system can include a minimal overall length compared to extension length and can allow for extension and axial rotation. In one embodiment, after implantation of the system in accordance with the principles of the present disclosure, a patient can be periodically placed in traction in an effort to lengthen the rod and to compensate for patient growth. In one embodiment, the rod automatically lengthens during patient activity. In one embodiment, fluoroscopy can be used to locate a drive hex of the system and a driver is percutaneously docked and rotated in either direction to lengthen the system. It is contemplated that components of the system may be coated with an antimicrobial agent to reduce the likelihood of infection.

In one embodiment, the spinal correction apparatus uses a cam to raise and lower an inner sleeve during rotation and may be direction independent. During upward motion of the inner sleeve, a carriage is engaged to a rack through the use of pawls. A pawl used in conjunction with the carriage slides past the rack of the sleeve during this upward motion. A spring is positioned between the pawls, which causes the pawls to engage onto their respective racks. On downward travel of the inner sleeve, a pawl is engaged to the rack of the sleeve and a pawl slides past the inner sleeve. The alternative action causes the carriage to travel upwards. When using traction to lengthen, both pawls will slide over the thread profile of the drive screw and past the racks of the sleeve and inner sleeve. This configuration allows the carriage to travel upward.

In one embodiment, the spinal correction apparatus includes a drive system that uses a worm drive and a pawl mechanism to raise and lower the carriage. Axial rotation of the worm drive causes a drive screw to rotate about its axis, for example, about 90 degrees relative to the worm gear axis, via their engaged teeth, which follows the thread pitch of the drive screw and in turn forces the carriage to translate either up or down depending on the rotation of the worm drive. A plunger and coil spring are positioned between a helical pawl and a housing, which causes the helical pawl to engage the drive screw thread. When the drive screw is rotated, the helical pawl is forced to follow the thread pitch of the drive screw. Upward and downward motion is transmitted through the helical pawl to the carriage. For example, after implantation, a patient is periodically placed in traction in an effort to lengthen the rod and compensate for patient growth. The rod automatically lengthens during patient activity. If lengthening cannot be achieved by placing the patient in traction, fluoroscopy can be used to locate the drive hex and a driver is percutaneously docked and rotated to lengthen the construct. Rotating the drive mechanism in one direction will lengthen the rod and rotating the drive mechanism in the other direction will shorten the rod.

In one embodiment, the spinal correction apparatus lengthens using only traction and the system may extend, for example, to about 100 mm. The apparatus comprises an elliptical body with dimensions including but not limited to about 12 mm by about 9.5 mm. The system may also comprise a spring-loaded plunger.

In one embodiment, the spinal correction apparatus lengthens using only a drive mechanism; for example, a drive hex. The apparatus may extend including but not limited to about 100 mm. The apparatus may comprise an elliptical body with the dimensions including but not limited to about 14 mm by about 8 mm.

It is contemplated that one or all of the components of the surgical system may be disposable, peel-pack, pre-packed sterile devices. One or all of the components of the system may be reusable. The system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Referring now to FIGS. 1-13, there is illustrated components of a surgical system including, for example, a spinal correction apparatus 40 in accordance with the principles of the present disclosure.

The components of the surgical system can be fabricated from biologically acceptable materials suitable for medical applications, including metals, synthetic polymers, ceramics, bone material, tissue and/or their composites, depending on the particular application and/or preference of a medical practitioner. For example, the components of the surgical system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the surgical system may have material composites, including the above materials, to achieve various desired characteristics such as strength, rigidity, elasticity, compliance, biomechanical performance, durability and radiolucency or imaging preference. The components of the surgical system, individually or collectively, may also be fabricated from a heterogeneous material such as a combination of two or more of the above-described materials. The components of the surgical system may be monolithically formed, integrally connected or include fastening elements and/or instruments, as described herein.

The components of the surgical system including spinal correction apparatus 40 are employed, for example, with an open or mini-open, minimal access and/or minimally invasive including percutaneous surgical technique to attach a longitudinal element to a spine that has a spinal disorder. In one embodiment, the longitudinal element may be affixed to a selected section of the spine and/or other anatomy while allowing for growth and adjustments to a concave side of a plurality of vertebrae for a correction treatment to treat various spine pathologies, such as, for example, adolescent idiopathic scoliosis and Scheuermann's kyphosis.

Spinal correction apparatus 40 includes a body, such as, for example, outer sleeve 42 that defines a longitudinal axis a. Outer sleeve 42 extends between a first end 44 and a second end 46. Sleeve 42 has a cylindrical cross sectional configuration. It is envisioned that sleeve 42 may have an oval, oblong, triangular, square, polygonal, irregular, uniform, non-uniform, offset, staggered, undulating, arcuate, variable and/or tapered configuration. Sleeve 42 includes an outer surface 48. It is contemplated that all or only a portion of outer surface 48 may have alternate surface configurations to enhance fixation with tissue such as, for example, rough, arcuate, undulating, mesh, porous, semi-porous, dimpled and/or textured according to the requirements of a particular application. Sleeve 42 includes an inner surface 50 that defines a cavity 52. Cavity 52 has an oval cross sectional configuration. It is envisioned that cavity 52 may have alternate cross sectional configurations such as, for example, oblong, triangular, square, polygonal, irregular, uniform, non-uniform, offset, staggered, undulating, arcuate, variable and/or tapered configuration. Cavity 52 is configured for disposal of the components of spinal correction apparatus 40. It is envisioned that sleeve 42 may include an opening for observing the components located within sleeve 42.

End cap 54 is disposed at first end 44 of sleeve 42 and includes a centrally located opening 56. Opening 56 is configured for movable disposal of a first longitudinal element, such as, for example, a rod 120, discussed below. End cap 58 is disposed at second end 46 of sleeve 42 and includes a centrally located opening 60. Opening 60 is configured for disposal of a second longitudinal element, such as, for example, a rod 122, discussed below. It is envisioned that openings 56, 60 may have alternate cross sectional configurations such as, for example, circular, oval, oblong, triangular, square, polygonal, irregular, uniform, non-uniform, offset, staggered, undulating, arcuate, variable and/or tapered configuration.

A ratchet 62 is connected to sleeve 42. Ratchet 62 is disposed within cavity 52 of sleeve 42. Ratchet 62 includes a rack 64 mounted to inner surface 50. Rack 64 extends between a first end 66 and a second end 68. First end 66 includes a connecting portion, such as, for example transverse flange 70. Flange 70 has an opening configured for support and slidable movement of rod 120. Flange 70 is mounted adjacent end 44 with end cap 54. Rack 64 includes gear teeth 72 disposed axially between ends 66, 68.

Ratchet 62 includes a second rack 74 formed within inner surface 50. Second rack 74 extends between a first end and a second end. Second rack 74 includes gear teeth 80 disposed axially along inner surface 50. It is contemplated that rack 74 may be a separate component and mounted to inner surface 50.

Ratchet 62 includes a carriage assembly comprising a carriage 82. Carriage 82 defines surface 84 that defines a cavity for disposal of pawls 88, 90. Pawl 88 includes gear teeth 92. Gear teeth 92 are configured for engagement with gear teeth 80 of second rack 74. Pawl 90 includes gear teeth 94. Gear teeth 94 are configured for engagement with gear teeth 72 of first rack 64. Pin 96 connects pawls 88, 90 to carriage 82.

Pawls 88, 90 are rotatable relative to carriage 82 such that pawls 88, 90 pivot about pin 96 respectively. Pawl 88 pivots about pin 96 to facilitate releasable engagement of teeth 92 with teeth 80 and pawl 90 pivots about pin 96 to facilitate releasable engagement of teeth 72 with teeth 94 to advance carriage 82 in at least one axial direction. It is contemplated that a biasing member may be connected to pawls 88, 90 to facilitate pivotable movement of pawls 88, 90 relative to carriage 82. In one embodiment, the biasing member includes a spring.

Second end 68 includes a housing 100. Housing 100 includes an inner surface 102 that defines a transverse channel 104. Channel 104 has a non-circular configuration, such as, for example, substantially elliptical for movable disposal of an actuator 106. Channel 104 may have various configurations, such as, for example, those alternatives described herein.

Actuator 106 includes a cam 108. Cam 108 has an outer surface 110 and a cylindrical configuration. Cam 108 is rotatable within channel 104 such that outer surface 110 engages inner surface 102 to cause axial translation of housing 100. Cam 108 includes a socket 112 having a hexagonal configuration. Socket 112 is configured for engagement with an instrument, as described below. Socket 112 is offset from a central transverse axis of cam 108 such that cam 108 is rotatable to follow an off center transverse axis path relative to the central transverse axis. Actuator 106 includes washer 114 that includes an inner surface 116. Washer 114 is disposed with cam 108, which are mounted with opening 118 of sleeve 42.

Actuator 106 is disposed with sleeve 42 and is connected to ratchet 62 to facilitate incremental movement of rod 120 relative to sleeve 42 in at least one axial direction. Actuator 106 is rotatable in a first direction, such as, for example, a clockwise direction and a second direction, such as, for example, a counter clockwise direction in order to facilitate movement of rod 120 in at least one axial direction, such as, for example, a first axial direction, as shown by arrow B in FIG. 3.

Figure 8:
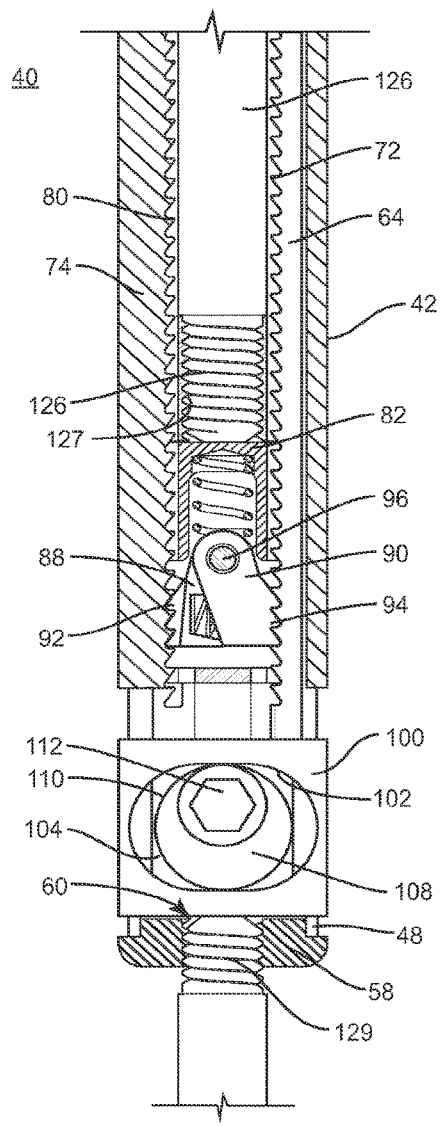
FIG. 8 is a cross sectional break away view of the system shown in FIG. 1.

Rod 120 extends between a first end 124 and a second end 126 (FIG. 8). Rod 120 is inserted into sleeve 42 through opening 56 of end cap 54. Rod 120 is disposed in a telescopic configuration within sleeve 42. Second end 126 includes an outer surface that is threaded with a threaded cavity 127 (FIG. 8) of carriage 82 to facilitate movement of rod 120 relative to sleeve 42, as will be described.

Spinal correction apparatus 40 includes a second longitudinal element, such as for example, rod 122. Rod 122 extends between a first end 128 and a second end 129 (FIG. 8). Rod 122 is inserted into sleeve 42 through opening 60 of end cap 58.

Rods 120, 122 can have a uniform thickness/diameter. It is envisioned that rods 120, 122 may have various surface configurations, such as, for example, rough, threaded for connection with surgical instruments, arcuate, undulating, dimpled, polished and/or textured according to the requirements of a particular application. It is contemplated that the thickness defined by rods 120, 122 may be uniformly increasing or decreasing, or have alternate diameter dimensions along their length. It is further contemplated that rods 120, 122 may have various cross section configurations, such as, for example, oval, oblong, triangular, rectangular, square, polygonal, irregular, uniform, non-uniform, variable and/or tapered. It is contemplated that rods 120, 122 may have various lengths, according to the requirements of a particular application.

Figure 5:
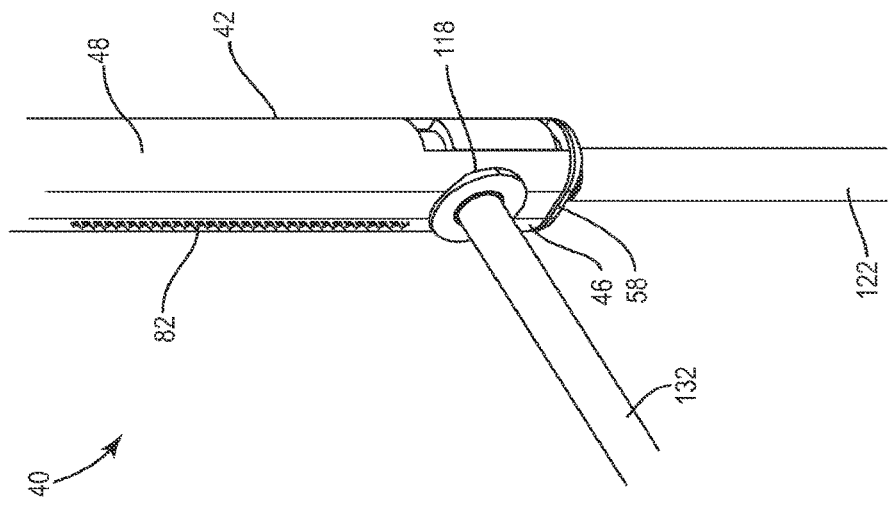
FIG. 5 is a perspective break away view of the system and tool shown in FIG. 4.
Figure 4:
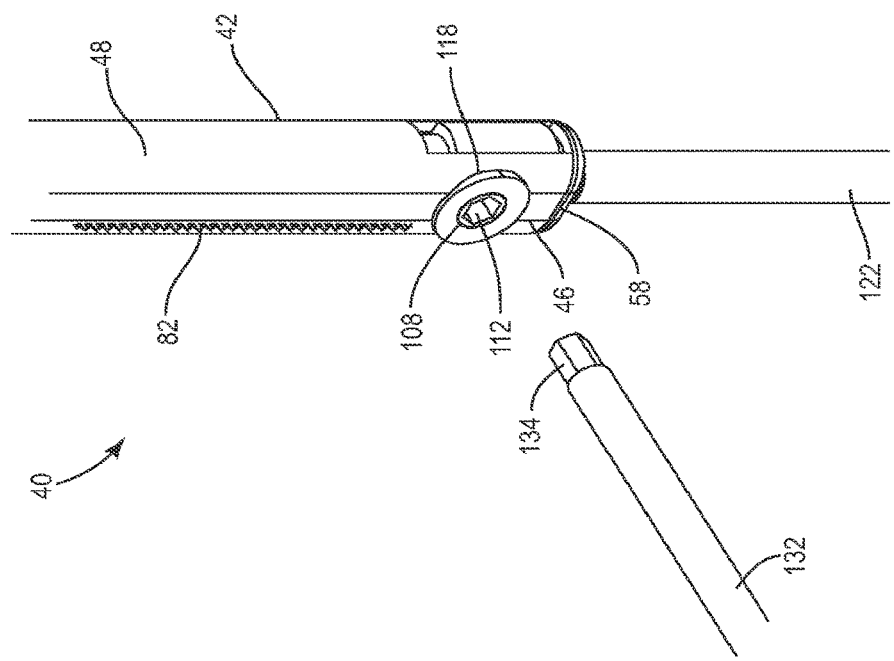
FIG. 4 is a perspective break away view of the system shown in FIG. 1 including a tool.

In operation, as shown in FIGS. 4-10, the system including spinal correction apparatus 40 includes an instrument, such as, for example, a drive tool 132, as shown in FIGS. 4-6. Drive tool 132 is manipulated to engage cam 108 of actuator 106 and rotated to facilitate incremental movement of rod 120 relative to sleeve 42 in at least one axial direction. Drive tool 132 includes a tip 134 having a hexagonal cross section configuration for mating with socket 112. It is contemplated that tip 134 may have alternative configurations, such as, for example, those alternatives described herein.

Tip 134 is inserted into opening 118 of sleeve 42 and passes through inner surface 116 of washer 114, as shown in FIGS. 7-8. Cam 108 is disposed in a first orientation in channel 104. Carriage 82 is disposed adjacent second end 46 and pawls 88, 90 are disposed to engage racks 74, 64, respectively, in a gear mesh fixation.

Tip 134 is caused to engage socket 112 of cam 108 and drive tool 132 is rotated in a clockwise direction, as shown by arrow A in FIG. 7. Drive tool 132 rotates cam 108 within channel 104 such that the circular configuration of outer surface 110 engages the non-circular configuration of inner surface 102 along an off center path of rotation. Engagement of outer surface 110 with inner surface 102 drives housing 100 towards first end 44 and into engagement with carriage 82. Carriage 82 is driven in the first axial direction, as shown by arrow B, towards first end 44 such that teeth 92 advance along teeth 80 and teeth 94 advance along teeth 72. Pawls 88, 90 are biased outwardly such that the gear teeth are disposed in a releasable mesh fixation and a fixed position with racks 74, 64.

Figure 9:
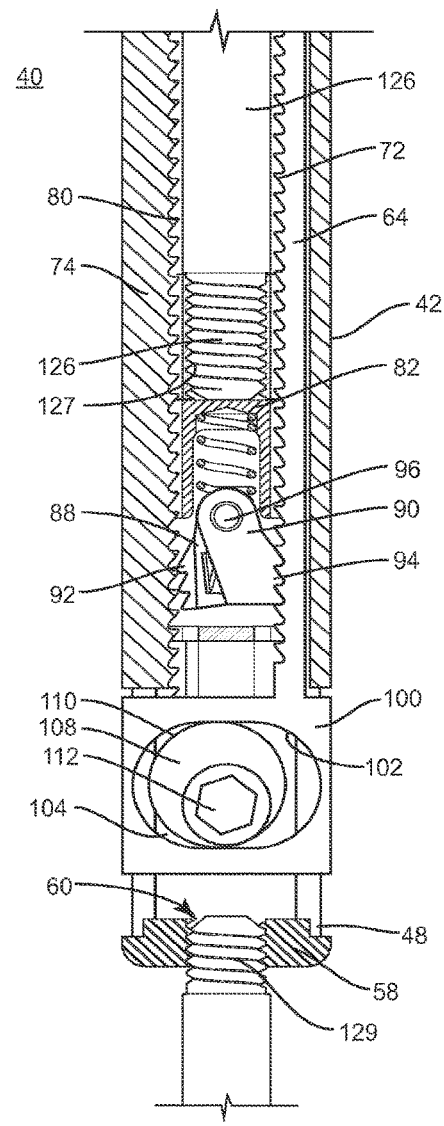
FIG. 9 is a cross sectional break away view of the system shown in FIG. 1.
Figure 10:
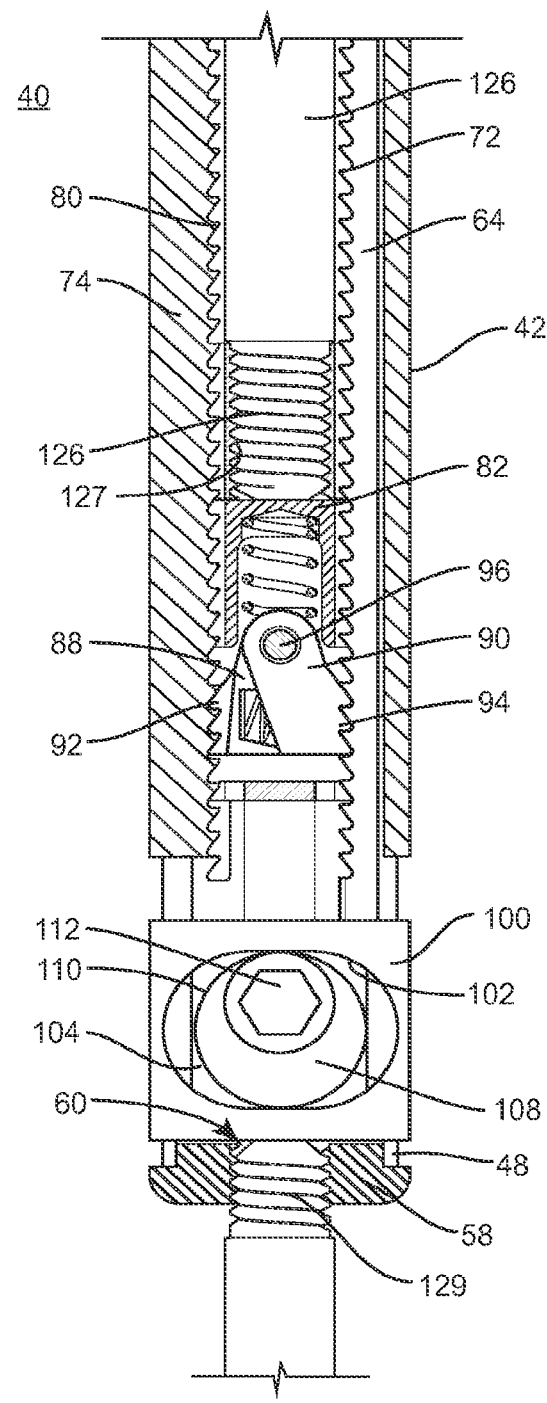
FIG. 10 is a cross sectional break away view of the system shown in FIG. 1.

As carriage 82 advances in the direction of arrow B, pawls 88, 90 become releasably fixed in an advanced position with racks 74, 64 such that the respective rack and pawl teeth are engaged, as shown in FIGS. 9-10. As drive tool 132 is further rotated, carriage 82 is further advanced in the direction shown by arrow B, via advancement of pawls 88, 90 with racks 74, 64 as described, and rod 120 is advanced in the direction shown by arrow B, according to the requirements of a particular application. This configuration facilitates incremental movement of rod 120 relative to sleeve 42 in the direction shown by arrow B. Movement of rod 120 relative to sleeve 42 expands the overall length of apparatus 40 to be used, for example, with a body invasive procedure for stabilization of vertebrae, initial implantation and/or to compensate for patient growth. In one embodiment, cam 108 may be rotated in a clockwise direction and a counterclockwise direction to advance rod 120 in the first axial direction. In one embodiment, rod 120 is advanced in the first axial direction only. In one embodiment, movement of rod 120 relative to sleeve 42 expands the overall length of spinal correction apparatus to compensate for axial rotation of a body.

Figure 11:
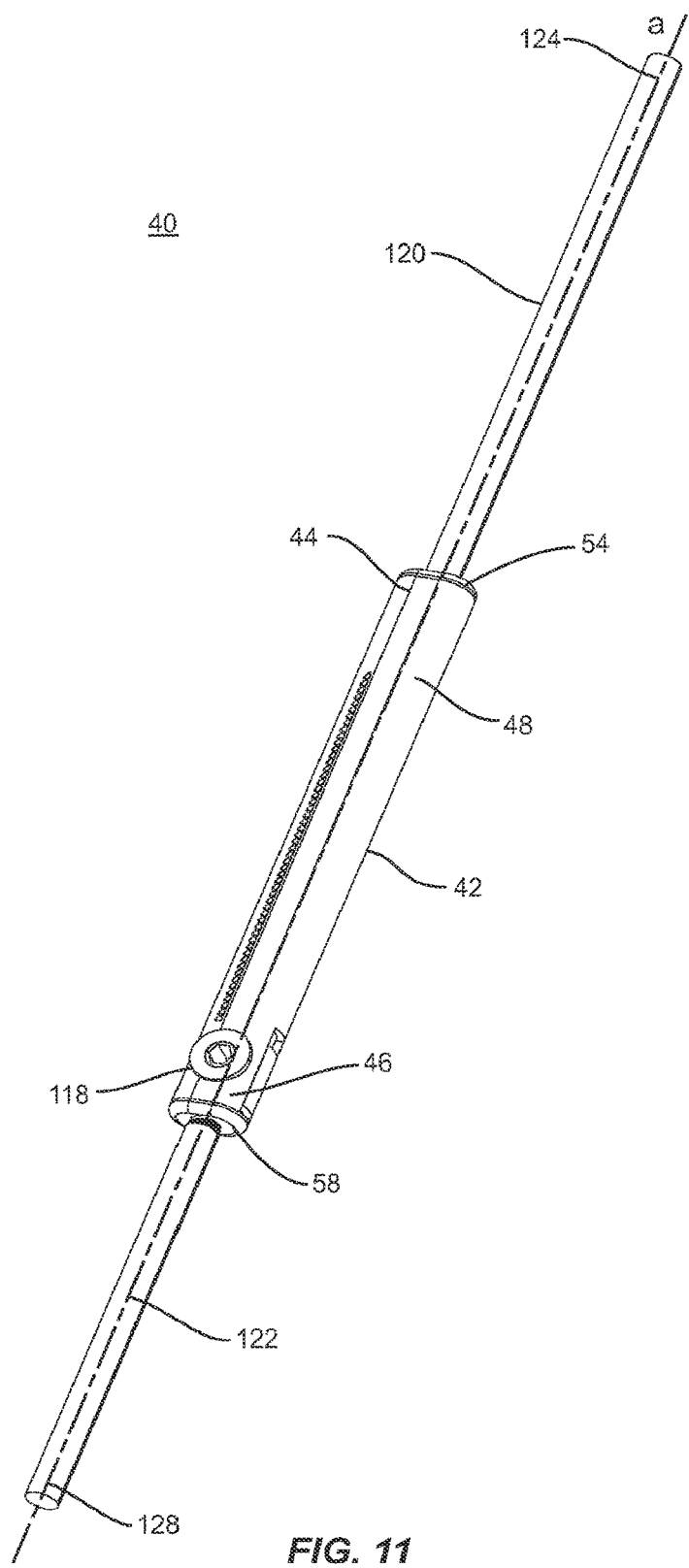
FIG. 11 is a perspective view of the system shown in FIG. 1.
Figure 12:
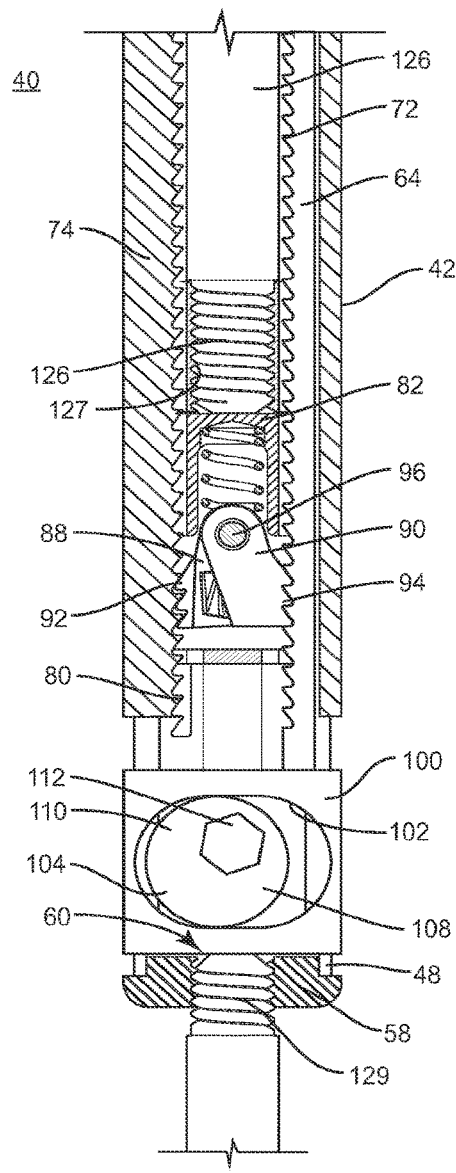
FIG. 12 is a cross sectional break away view of the system shown in FIG. 1.
Figure 13:
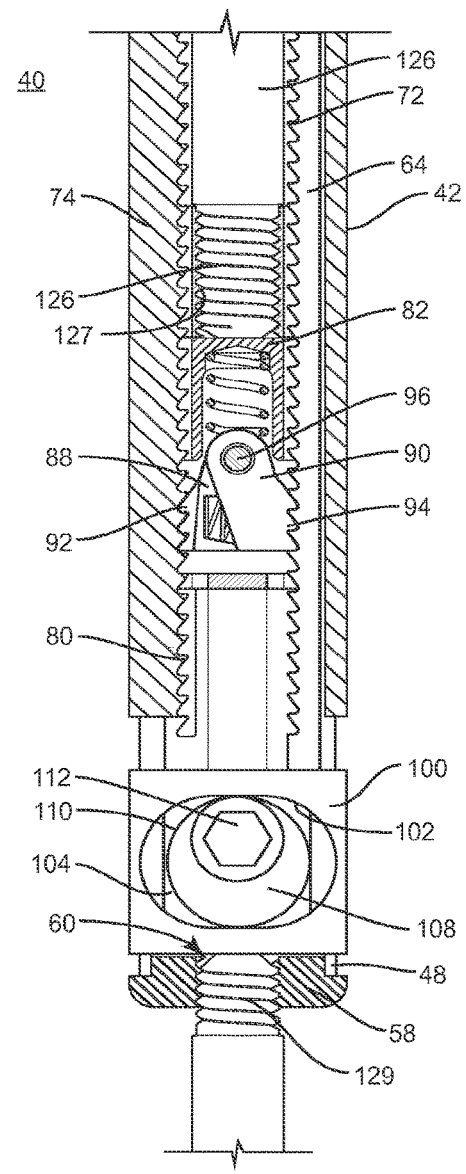
FIG. 13 is a cross sectional break away view of the system shown in FIG. 1.

Spinal correction apparatus 40 is also configured for non-invasive lengthening to compensate for patient growth, as shown in FIGS. 11-13. For example, during patient growth, a force, such as, for example, an expansion force, due to separation of anatomical body portions attached to apparatus 40, is applied to rod 120 and/or rod 122 that causes dynamic incremental movement of rod 120, independent of actuator 106, relative to sleeve 42 in the first axial direction, as shown by arrow B in FIG. 11. In one embodiment, dynamic incremental movement of rod 120 and/or rod 122 is responsive to, caused by and/or associated with motion of a spine and adjacent anatomical portions of a body of a patient. In one embodiment, such motion includes motion of the spine and adjacent anatomical portions due to the natural load bearing and dynamic characteristics of the spine, which may include flexion, extension, rotation and lateral bending. In one embodiment, such motion includes motion of the spine and adjacent anatomical portions due to external loads, which may include axial, shear, linear, non-linear, angular, torsional, compressive and/or tensile loads, applied to the body of the patient.

Upon application of the expansion force to first end 124 of rod 120, carriage 82 is drawn in the first axial direction, as shown by arrow B, towards first end 44 such that teeth 92 advance along teeth 80 and teeth 94 advance along teeth 72, as shown in FIGS. 12-13. Pawls 88, 90 are biased outwardly such that the gear teeth are disposed in a releasable mesh fixation and a fixed position with racks 74, 64. In one embodiment, the forces are applied to rod 122.

As carriage 82 is drawn and advances in the direction of arrow B, pawls 88, 90 become releasably fixed in an advanced position with racks 74, 64 such that the respective rack and pawl teeth are disposed in a releasable mesh fixation. Carriage 82 is advanced in the direction shown by arrow B, via advancement of pawls 88, 90 with racks 74, 64 as described, and rod 120 is advanced in the direction shown by arrow B, according to the expansion force, such as, for example, an amount of growth between the anatomical portions connected to spinal correction apparatus 40. The mesh engagement of the gear teeth of pawls 88, 90 with racks 74, 64 prevents contraction and/or axial movement of rod 120 relative to sleeve 42 in a direction opposite to the first axial direction and permits further expansion and/or advancement of rod 120 relative to sleeve 42, in the first axial direction, according to other forces applied to spinal correction apparatus 40 and/or subsequent patient growth. This configuration provides dynamic incremental movement of rod 120 relative to sleeve 42 in the direction shown by arrow B, to be used, for example, for stabilization of vertebrae and non-invasive lengthening and/or compensation for patient growth.

In assembly, operation and use, a system including spinal correction apparatus 40, similar to that described above, is employed with a surgical procedure, such as, for example, a correction treatment to treat adolescent idiopathic scoliosis and/or Scheuermann's kyphosis of a spine. It is contemplated that one or all of the components of the spinal correction system can be delivered or implanted as a pre-assembled device or can be assembled in situ. The system including spinal correction apparatus 40 may be completely or partially revised, removed or replaced.

For example, spinal correction apparatus 40, described above, can be employed with a surgical correction treatment of an applicable condition or injury of an affected section of a spinal column and adjacent areas within a body, such as, for example, at least a first vertebra V1 and a second vertebra V2 of vertebrae V. It is envisioned that spinal correction apparatus 40 may be employed with one or a plurality of vertebrae.

In use, to treat a selected section of vertebrae V, a medical practitioner obtains access to a surgical site including vertebrae V in any appropriate manner, such as through incision and retraction of tissues. It is envisioned that the spinal correction system can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of the system including spinal correction apparatus 40. A preparation instrument (not shown) can be employed to prepare tissue surfaces of vertebrae V, as well as for aspiration and irrigation of a surgical region according to the requirements of a particular surgical application.

Figure 14:
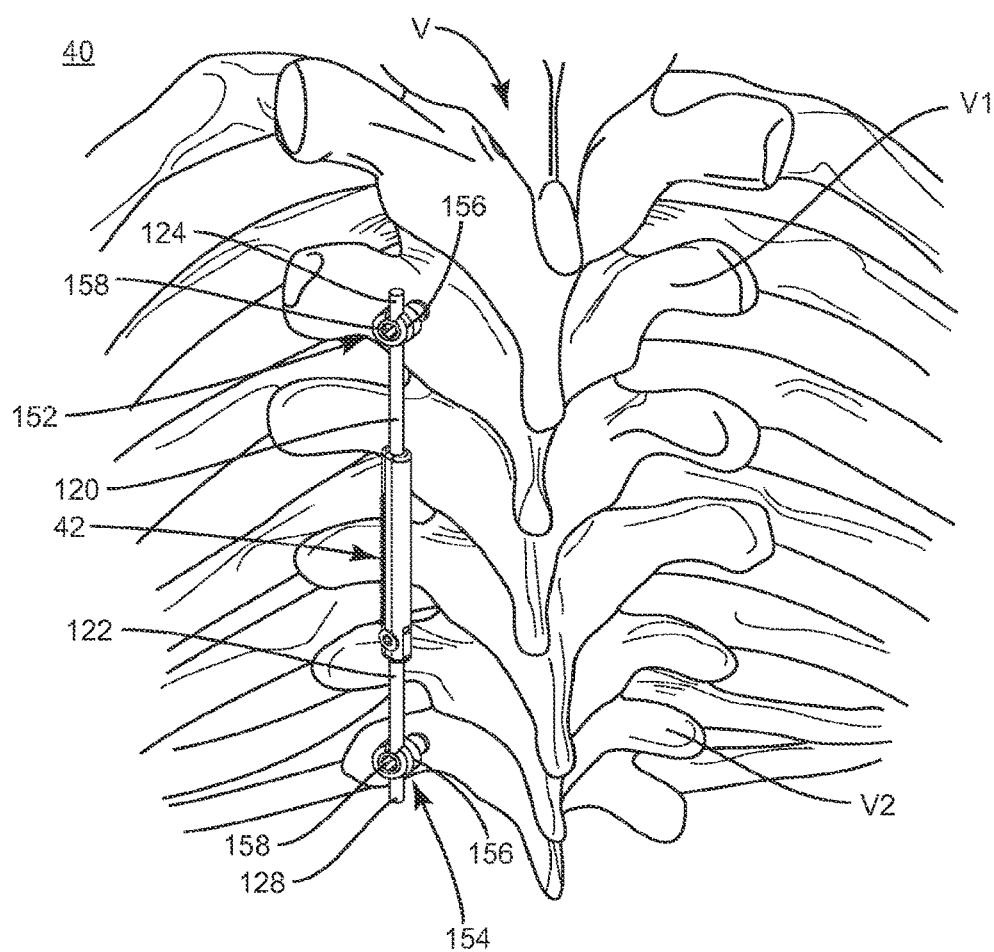
FIG. 14 is a perspective view of the system shown in FIG. 1, disposed with vertebrae.
Figure 15:
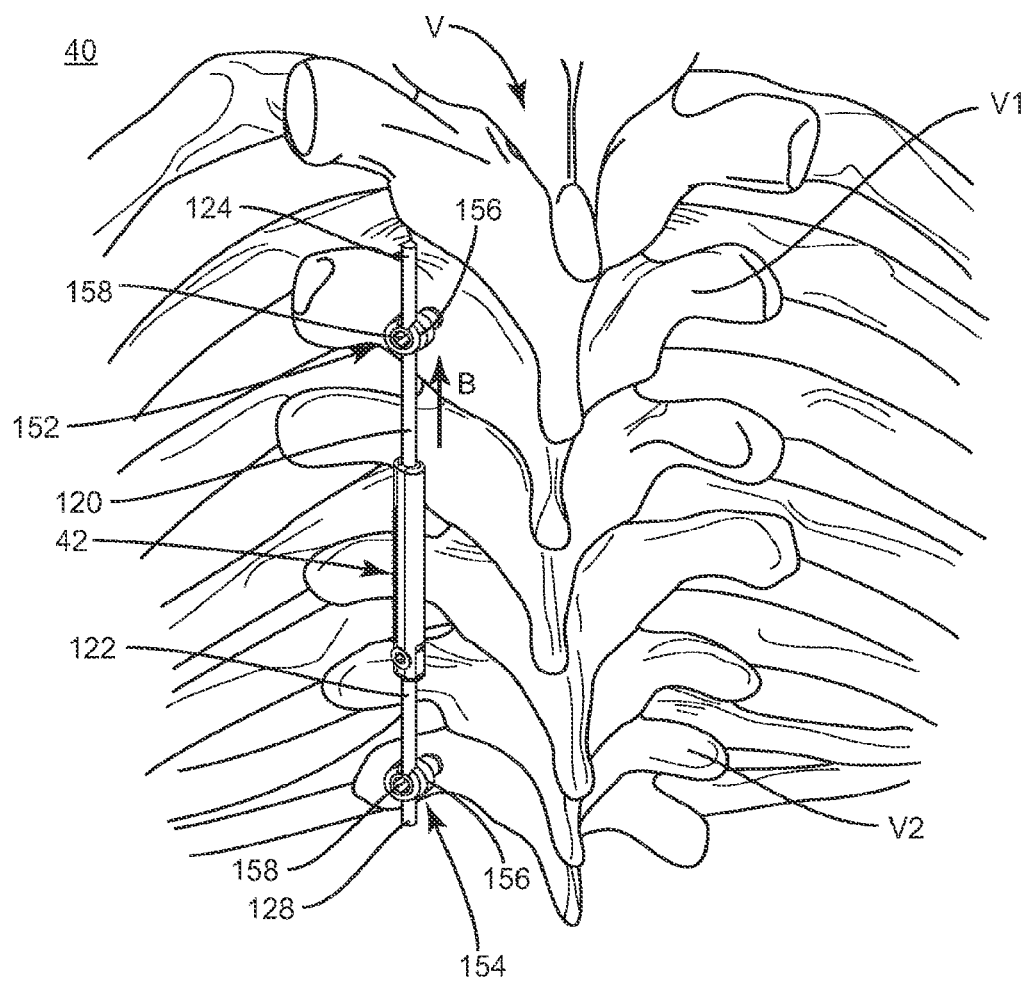
FIG. 15 is a perspective view of the system and vertebrae shown in FIG. 1.
Figure 16:
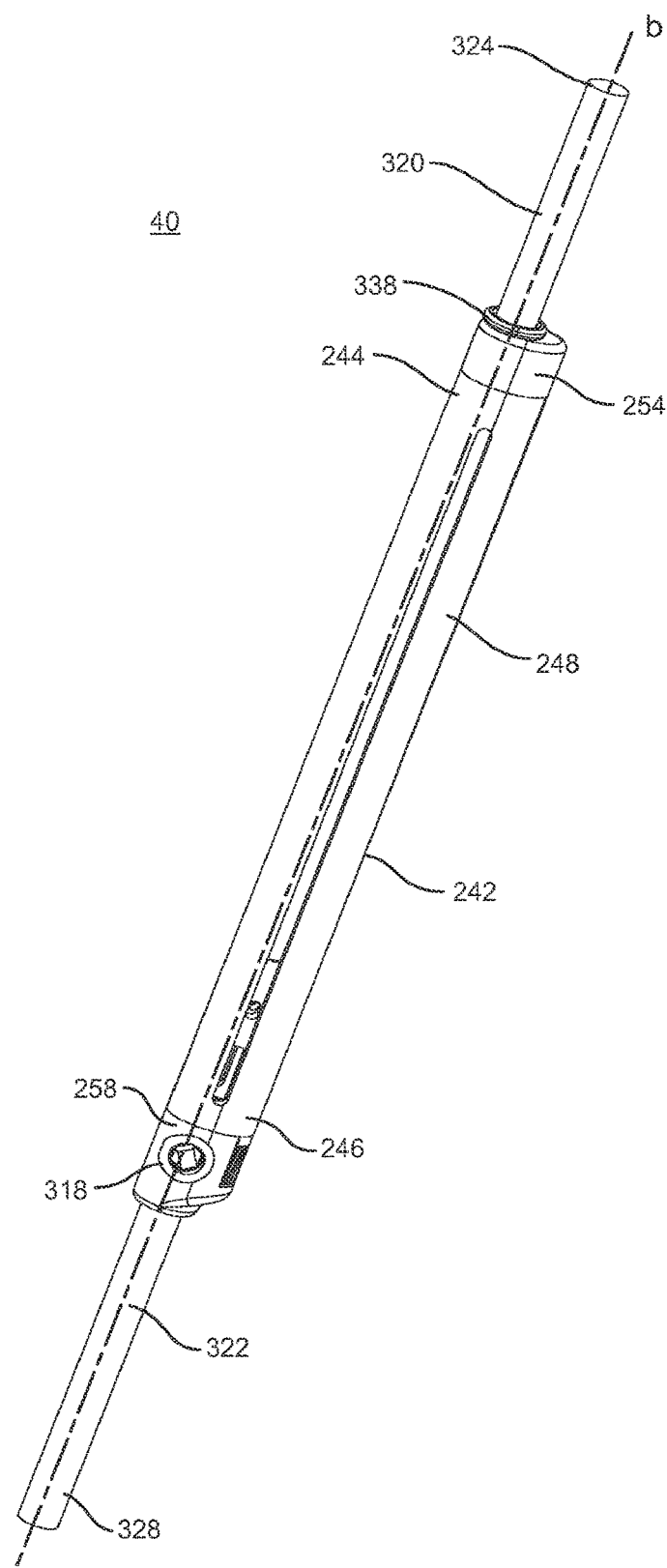
FIG. 16 is a perspective view of one particular embodiment of a system including a spinal correction apparatus in accordance with the principles of the present disclosure.
Figure 17:
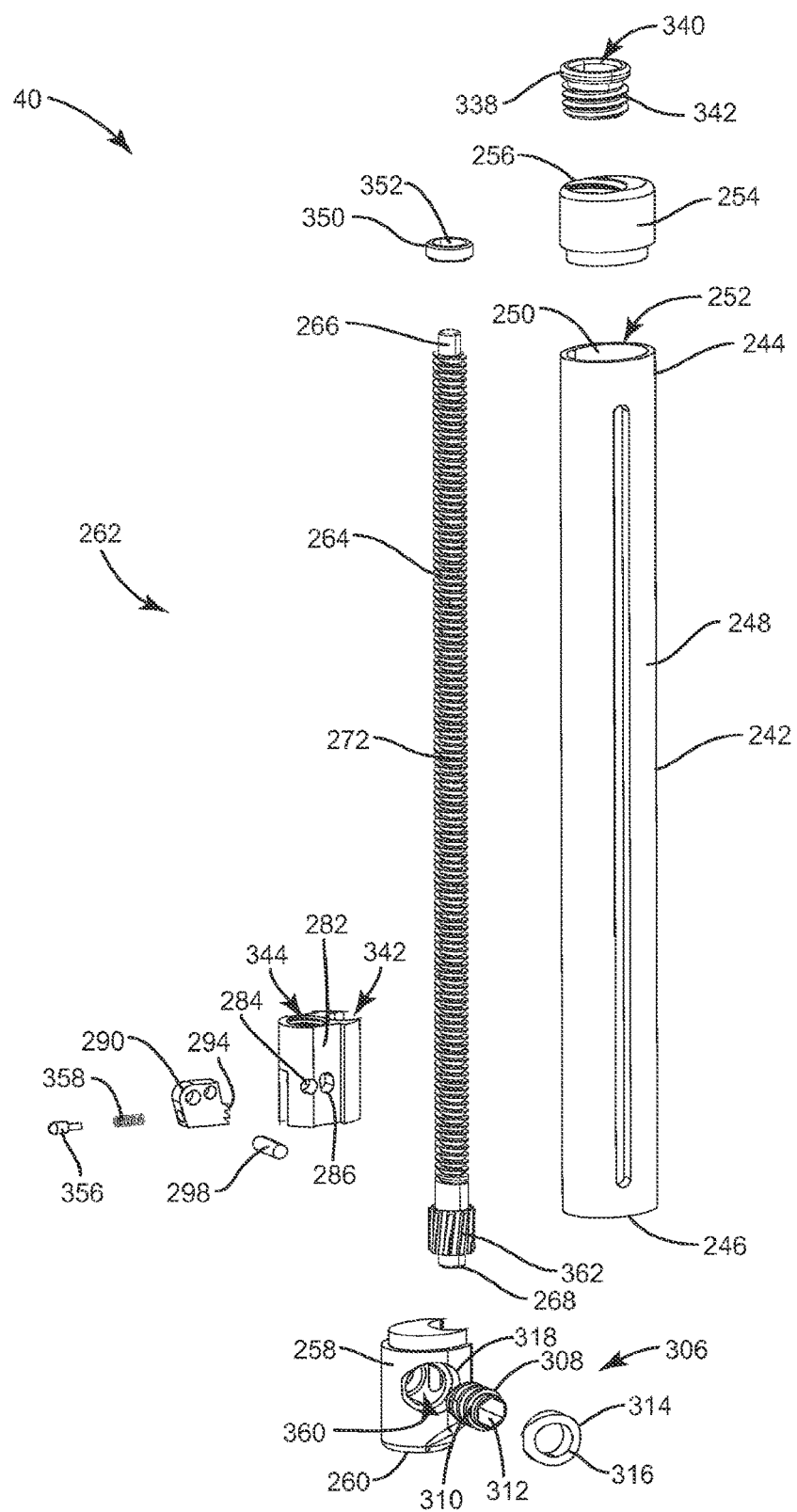
FIG. 17 is a perspective view of the components of the system shown in FIG. 16 with parts separated.
Figure 18:
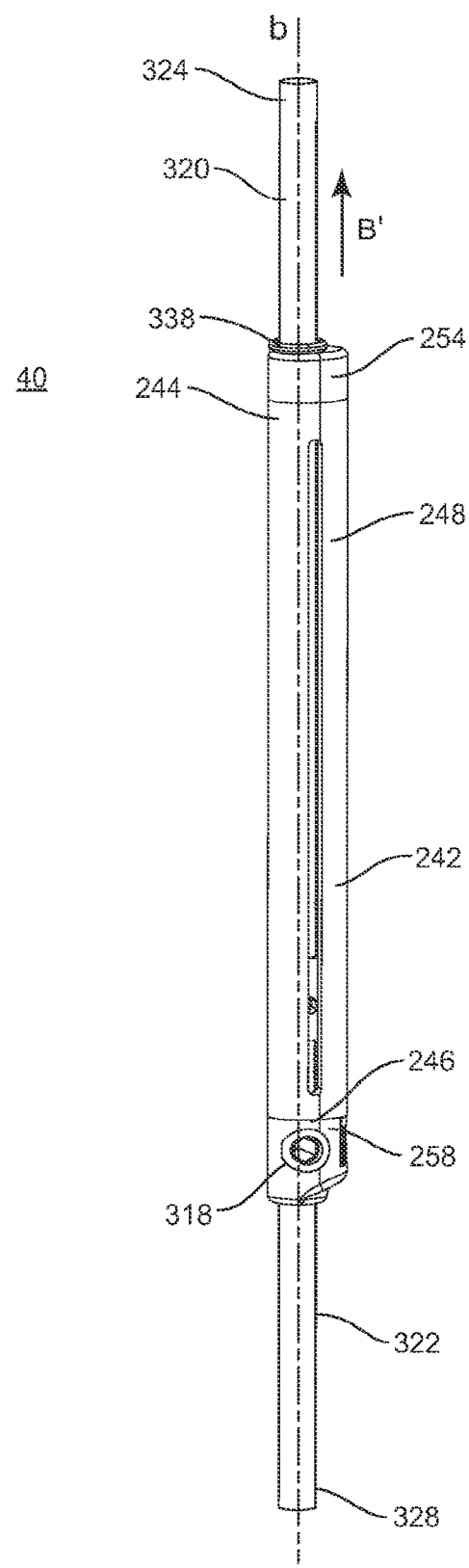
FIG. 18 is a perspective view of the system shown in FIG. 16.

Referring to FIGS. 14 and 15, a first fastening element, such as, for example, fixation screw assembly 152 is configured to attach first end 124 of rod 120 to vertebra V1. A second fastening element, such as, for example, fixation screw assembly 154 is configured to attach first end 128 of rod 122 to vertebra V2, which is spaced apart over vertebrae from vertebra V1. Pilot holes are made in vertebrae V1, V2 for receiving fixation screw assemblies 152, 154. Fixation screw assemblies 152, 154 include threaded bone engaging portions that are inserted or otherwise connected to vertebrae V1, V2, according to the particular requirements of the surgical treatment. Fixation screw assemblies 152, 154 each have a head 156 with a bore, or through opening and a setscrew 158, which is torqued on to ends 124, 128 to attach spinal correction apparatus 40 in place with vertebrae V, as will be described. It is envisioned that the fastening elements may include one or a plurality of hooks, anchors, tissue penetrating screws, mono-axial screws, multi-axial screws, expanding screws, wedges, buttons, clips, snaps, friction fittings, compressive fittings, expanding rivets, staples, nails, adhesives, fixation plates and/or posts. These fixation elements may be coated with an osteoinductive or osteoconductive material to enhance fixation, and/or include one or a plurality of therapeutic agents.

Upon fixation of spinal correction apparatus 40 with vertebrae V, as described, drive tool 132 is manipulated to engage cam 108 of actuator 106 and rotated to facilitate incremental movement of rod 120 relative to sleeve 42 in a first axial direction, as shown by arrow B in FIG. 15 and described above. Carriage 82 is advanced in the first axial direction such that pawls 88, 90 become releasably fixed in an advanced position with racks 74, 64 such that the respective rack and pawl teeth are engaged. Drive tool 132 is rotated to advance carriage 82 and expand rod 120 in the first axial direction, according to the requirements of a particular application. This configuration facilitates incremental movement of rod 120 relative to sleeve 42 in the first axial direction. Movement of rod 120 relative to sleeve 42 expands the overall length of spinal correction apparatus 40 for initial implantation and stabilization of vertebrae for a particular procedure. Upon completion of the procedure, the surgical instruments and assemblies are removed and the incision is closed. It is contemplated that spinal correction apparatus 40 may be adjusted in subsequent procedures with drive tool 132 engaging cam 108.

Upon implantation of spinal correction apparatus 40 and completion of the procedure, spinal correction apparatus 40 is configured for in situ, non-invasive lengthening to compensate for patient growth. For example, during patient growth, an expansion force, due to separation of vertebrae V1, V2 attached to spinal correction apparatus 40, is applied to rod 120 and/or rod 122 that causes dynamic incremental movement of rod 120, independent of actuator 106, relative to sleeve 42 in the first axial direction, as shown by arrow B in FIG. 15 and described above.

Upon application of the expansion force to first end 124 of rod 120, carriage 82 is drawn in the first axial direction and advances such that pawls 88, 90 become releasably fixed in an advanced position with racks 74, 64. The mesh engagement of the gear teeth of pawls 88, 90 with racks 74, 64 prevents contraction and/or axial movement of rod 120 relative to sleeve 42 in a direction opposite to the first axial direction and permits further expansion and/or advancement of rod 120 relative to sleeve 42, in the first axial direction, according to other forces applied to spinal correction apparatus 40 and/or subsequent patient growth. This configuration provides dynamic incremental movement of rod 120 relative to sleeve 42 in the first axial direction.

In one embodiment, ends 124, 128 can be attached from a selected portion of the spine to a selected portion of the ribs. In one embodiment, ends 124, 128 may be attached from the pelvic crest to a selected portion of the cervical spine. In one embodiment, ends 124, 128 can be attached from the pelvic crest to a selected portion of the ribs.

The system including spinal correction apparatus 40 can be made of radiolucent materials such as polymers. Radiomarkers may be included for identification under x-ray, fluoroscopy, CT or other imaging techniques. It is envisioned that the use of microsurgical and image guided technologies may be employed to access, view and repair spinal deterioration or damage, with the aid of the system including spinal correction apparatus 40.

It is contemplated that the components of the system including spinal correction apparatus 40 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. It is further contemplated that the components of the system including spinal correction apparatus 40 and method of use may be used to prevent or minimize curve progression in individuals of various ages.

In one embodiment, as shown in FIGS. 16-29, the system comprising spinal correction apparatus 40, similar to the apparatus and methods described above with regard to FIGS. 1-15, includes a body, such as, for example, outer sleeve 242 that defines a longitudinal axis b. Outer sleeve 242 extends between a first end 244 and a second end 246. Sleeve 242 has a cylindrical cross sectional configuration and an outer surface 248. Sleeve 242 includes an inner surface 250 that defines a cavity 252. Cavity 252 has an oval cross section configuration. Cavity 252 is configured for disposal of the components of spinal correction apparatus 40.

End cap 254 is disposed at first end 244 of sleeve 242 and includes offset opening 256. Opening 256 is configured for movable disposal of a first longitudinal element, such as, for example, a rod 320, discussed below. End cap 258 is disposed at second end 246 of sleeve 242 and includes a centrally located opening 260. Opening 260 is configured for disposal of a second longitudinal element, such as, for example, a rod 322, discussed below.

A bushing 338 is threadingly disposed within end cap 254. Bushing 338 includes a centrally located opening 340. Opening 340 has a threaded exterior surface 342 for mounting with end cap 254. Bushing 338 is configured for movable disposal of rod 320.

A ratchet 262 is connected to sleeve 242. Ratchet 262 is disposed within cavity 252 of sleeve 242. Ratchet 262 includes a rack, such as, for example, a drive screw 264 mounted to inner surface 250. Drive screw 264 extends between a first end 266 and a second end 268. Drive screw 264 includes a thread form 272 disposed axially between ends 266 and 268. Thread form 272 has a pitch that causes axial movement of a carriage assembly therealong, discussed below.

Ratchet 262 includes the carriage assembly comprising a carriage 282. Carriage 282 includes surfaces 284, 286 that define cavities for support of at least one post, discussed below, which movably connects a pawl 290, described below, with carriage 282. Carriage 282 includes a cavity 344 that has a threaded surface 346. Cavity 344 is configured for disposal of rod 320 and threaded surface 346 engages second end 326 for fixation therewith.

Carriage 282 includes gear teeth 348 configured for engagement with drive screw 264. Gear teeth 348 movably engage thread form 272 for axial movement in at least one axial direction relative to sleeve 242 along the helical and/or spiral configuration of thread form 272. A thrust washer 350 is configured for disposal within end cap 258. Thrust washer 350 includes opening 352 configured for movable disposal of drive screw second end 268.

Pawl 290 includes gear teeth 294 configured for engagement with thread form 272. A pin 298 extends through cavity 284 and pawl 290 to connect pawl 290 to carriage 282. Pawl 290 is pivotable relative to carriage 282. Pawl 290 rotates relative to carriage 282 such that pawl 290 pivots about pin 298. Pawl 290 pivots about pin 298 to facilitate releasable engagement of teeth 294 with thread form 272.

Pawl 290 includes a transverse recess 354 configured for disposal of a plunger 356 and a spring 358. Plunger 356 and spring 358 are disposed within transverse recess 354 to facilitate biased movement of pawl 290 into engagement with thread form 272. Spring 358 biases plunger 356 against the wall of sleeve 242 such that pawl pivots about pin 298 and gear teeth 294 are forced into a releasable mesh fixation and a fixed position with thread form 272.

Actuator 306 includes worm gear 308. Worm gear 308 has an outer threaded surface 310. Worm gear 308 is rotatable within a channel 360 of an end cap 258 such that outer threaded surface 310 engages with gear teeth 362 at an enlarged second end 268 of drive screw 264. End cap 258 defines a cavity that supports carriage 282 and drive screw 264. Worm gear 308 includes socket 312 having a hexagonal configuration. Socket 312 is configured for engagement with an instrument, as described below. Actuator 306 includes washer 314 having an opening 316. Washer 314 is disposed with worm gear 308, which are both mounted within channel 360 of end cap 258.

Actuator 306 is disposed within channel 360 and is connected to ratchet 262 to facilitate incremental movement of rod 320 relative to sleeve 242 in at least one axial direction. Actuator 306 is rotatable in a first direction, such as, for example, a clockwise direction and a second direction, such as, for example, a counter clockwise direction to facilitate movement of rod 320 in at least one axial direction, such as, for example, a first axial direction, as shown by arrow B' in FIG. 18.

Rod 320 extends between a first end 324 and a second threaded end 326. Rod 320 is inserted into sleeve 242 through bushing 338 and end cap 254. Second end 326 is fixed with carriage 282 in a threaded engagement. Rod 320 is disposed in a telescopic configuration within sleeve 242. Spinal correction apparatus 40 includes a second longitudinal element, such as, for example, rod 322. Rod 322 extends between a first end 328 and a second end (not shown). Rod 322 is inserted into sleeve 242 through end cap 258.

In operation, as shown in FIGS. 19-29, the system including spinal correction apparatus 40 includes an instrument, such as, for example, a drive tool 332. Drive tool 332 is manipulated to engage worm gear 308 and rotated to facilitate incremental movement of rod 320 relative to sleeve 242 in at least one axial direction. Drive tool 332 includes a tip 334 having a hexagonal cross section configuration for mating with socket 312.

Tip 334 is inserted into opening 318 of end cap 258 and passes through opening 316 of washer 314, as shown in FIGS. 19-20. Worm gear 308 is disposed in a first orientation with gear teeth 362 of enlarged second end 268 within end cap 258. Carriage 282 is disposed adjacent second end 246 and pawl 290 is disposed to engage thread form 272 in a gear mesh fixation.

Figure 22:
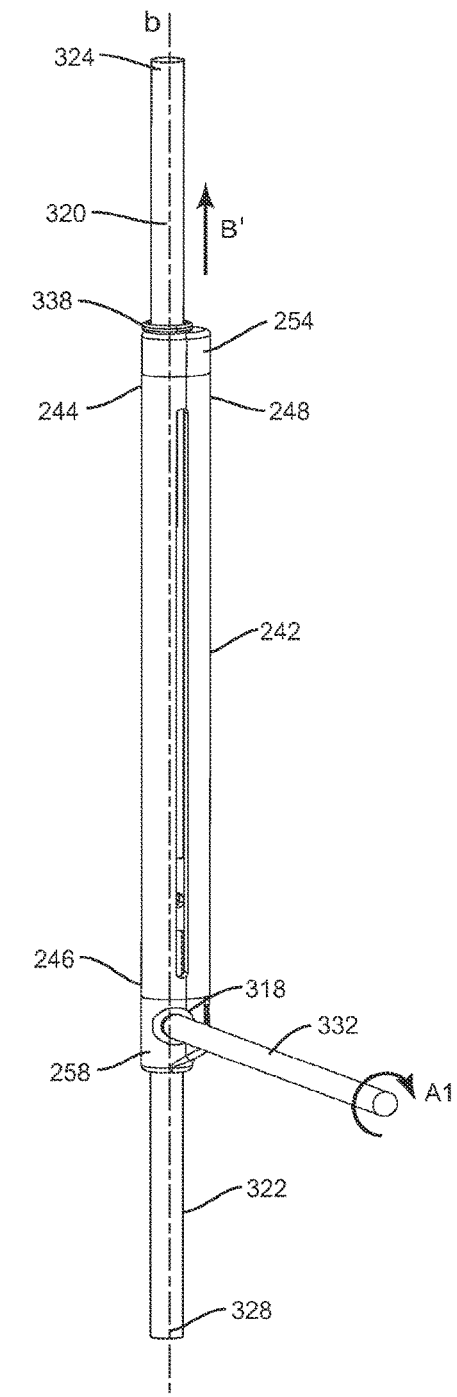
FIG. 22 is a perspective view of the system and tool shown in FIG. 19.
Figure 24:
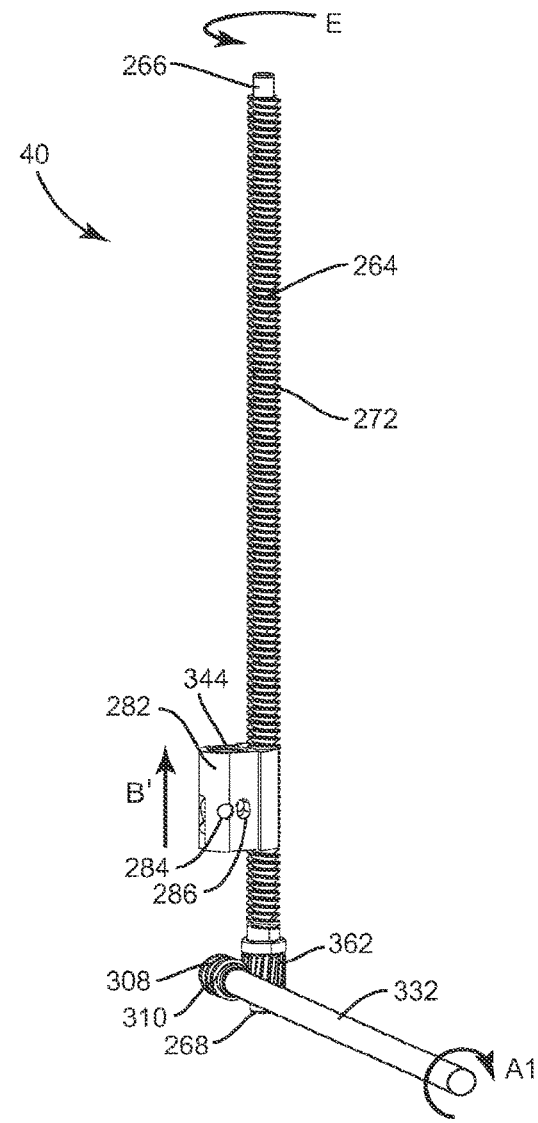
FIG. 24 is a perspective cutaway view of the system shown in FIG. 19.
Figure 25:
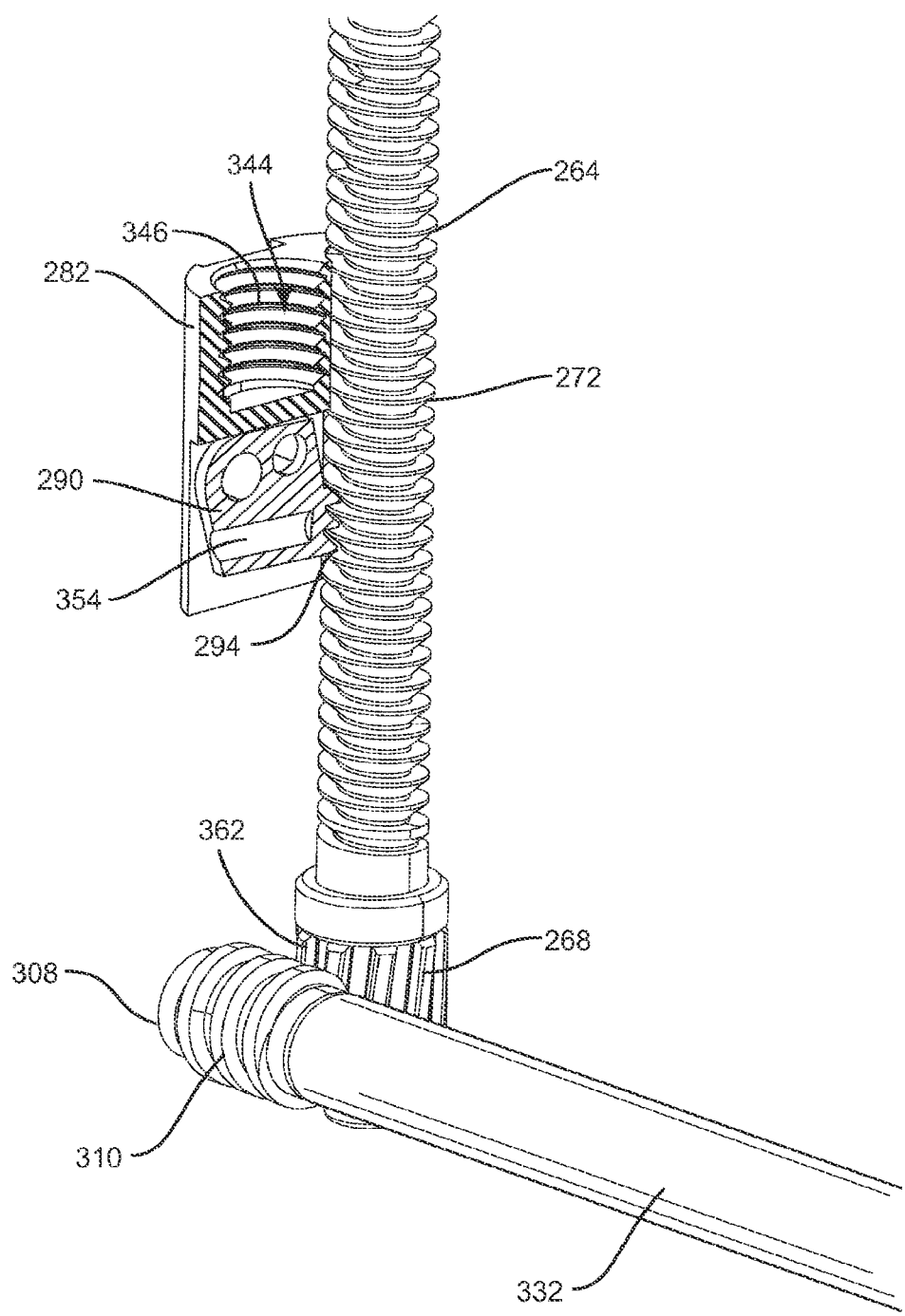
FIG. 25 is a perspective break away view of the system shown in FIG. 23.

Tip 334 is caused to engage socket 312 of worm gear 308 and drive tool 332 is rotated in a clockwise direction, as shown by arrow A1 in FIGS. 22 and 24. Drive tool 332 rotates worm gear 308 such that threaded surface 310 engages gear teeth 362 of second end 268 to rotate drive screw 264 in a first direction, such as, for example, a counterclockwise direction, as shown by arrow E in FIG. 24. Thread form 272 engages gear teeth 294 of pawl 290 along its helical configuration. Carriage 282 is driven in the first axial direction, as shown by arrow B', towards first end 244 such that teeth 294 advance axially in the first axial direction along the helical configuration of thread form 272. Pawl 290 is biased into engagement with thread form 272 to maintain engagement therebetween.

As drive tool 332 is further rotated, carriage 282 is further advanced, according to the requirements of a particular application. This configuration facilitates incremental movement of rod 320 relative to sleeve 242 in the first axial direction. Movement of rod 320 relative to sleeve 242 expands the overall length of apparatus 40 to be used, for example, with a body invasive procedure for stabilization of vertebrae, initial implantation and/or to compensate for patient growth.

Figure 21:
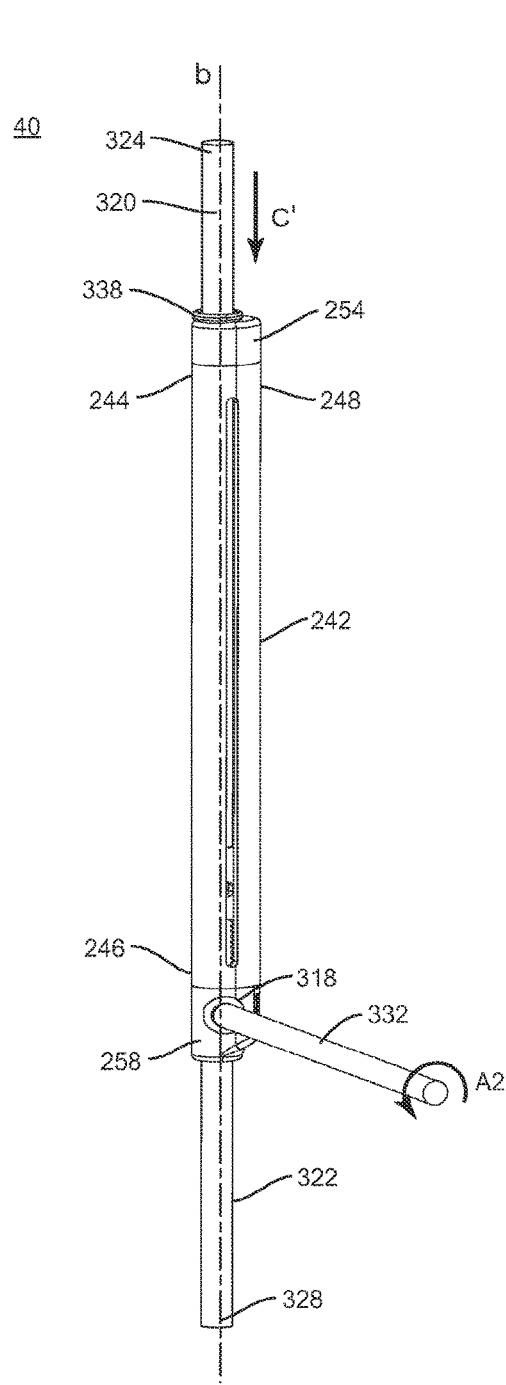
FIG. 21 is a perspective view of the system and tool shown in FIG. 19.
Figure 23:
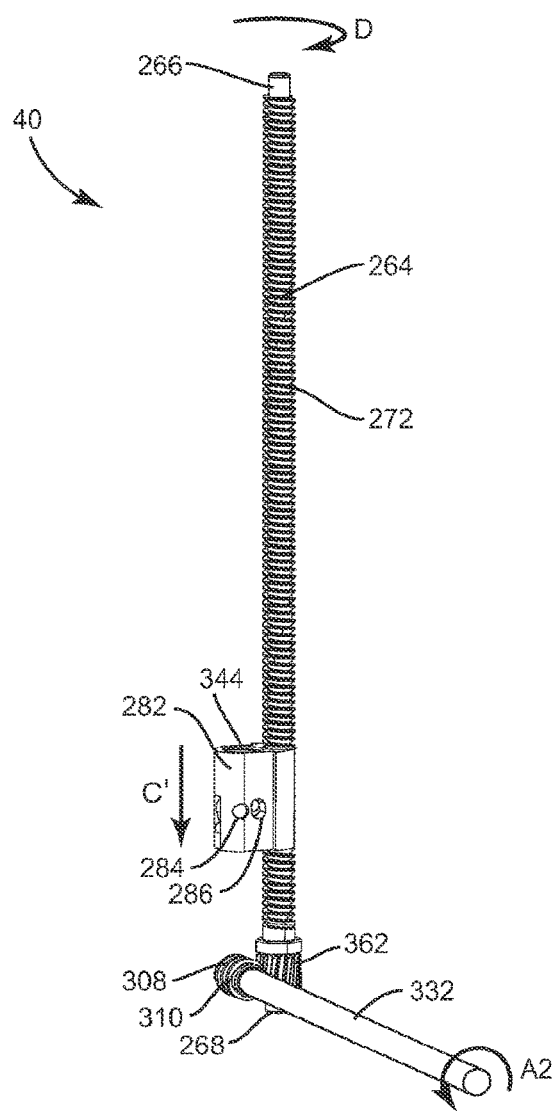
FIG. 23 is a perspective cutaway view of the system shown in FIG. 19.

Spinal correction apparatus 40 can be contracted such that tip 334 is caused to engage socket 312 of worm gear 308 and drive tool 332 is rotated in a counterclockwise direction, as shown by arrow A2 in FIGS. 21 and 23. Drive tool 332 rotates worm gear 308 such that threaded surface 310 engages gear teeth 362 of second end 268 to rotate drive screw 264 in a second direction, such as, for example, a clockwise direction, as shown by arrow D in FIG. 23. Thread form 272 engages gear teeth 294 of pawl 290 along its helical configuration. Carriage 282 is driven in a second axial direction, as shown by arrow C', towards second end 246 such that teeth 294 advance axially in the second axial direction along the helical configuration of thread form 272. Pawl 290 is biased into engagement with thread form 272 to maintain engagement therebetween. This configuration facilitates incremental movement of rod 320 relative to sleeve 242 in the second axial direction to compress and/or contract the overall length of spinal correction apparatus 40. In one embodiment, rod 320 is advanced in the first axial direction only or in the second axial direction only. In one embodiment, movement of rod 320 relative to sleeve 242 expands the overall length of apparatus 40 to compensate for axial rotation of a body.

Spinal correction apparatus 40 is also configured for non-invasive lengthening to compensate for patient growth, as shown in FIGS. 26-29. For example, during patient growth, a force, such as, for example, an expansion force, due to separation of anatomical body portions attached to spinal correction apparatus 40, is applied to rod 320 and/or rod 322 that causes dynamic incremental movement of rod 320, independent of actuator 306, relative to sleeve 242 in the first axial direction, as shown by arrow B' in FIG. 26, similar to that described above with regard to FIGS. 11-13.

Upon application of the expansion force to first end 324 of rod 320, carriage 282 is drawn in the first axial direction towards first end 244 such that teeth 294 advance axially in the first axial direction along the helical configuration of thread form 272 such that teeth 294 slide over thread form 272, as shown in FIGS. 12-13. Pawl 290 is biased into engagement with thread form 272. In one embodiment, the forces are applied to rod 322.

Figure 26:
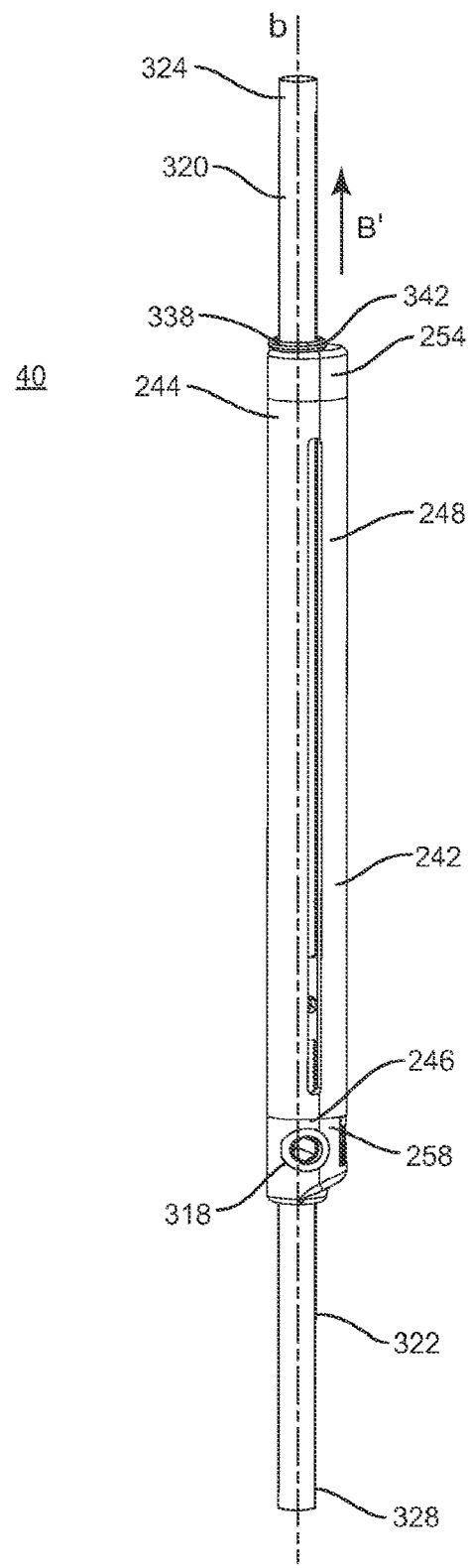
FIG. 26 is a perspective view of the system shown in FIG. 16.
Figure 27:
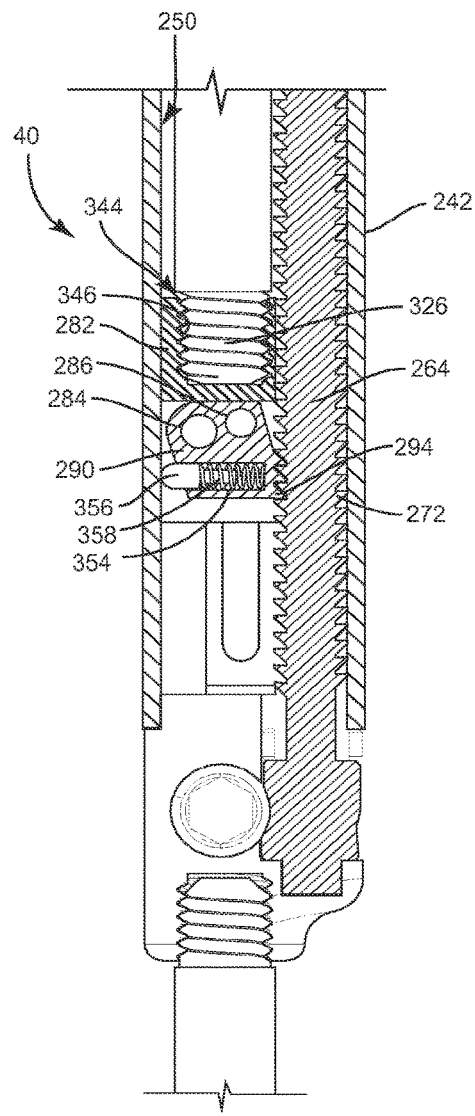
FIG. 27 is a cross sectional break away view of the system shown in FIG. 16.
Figure 28:
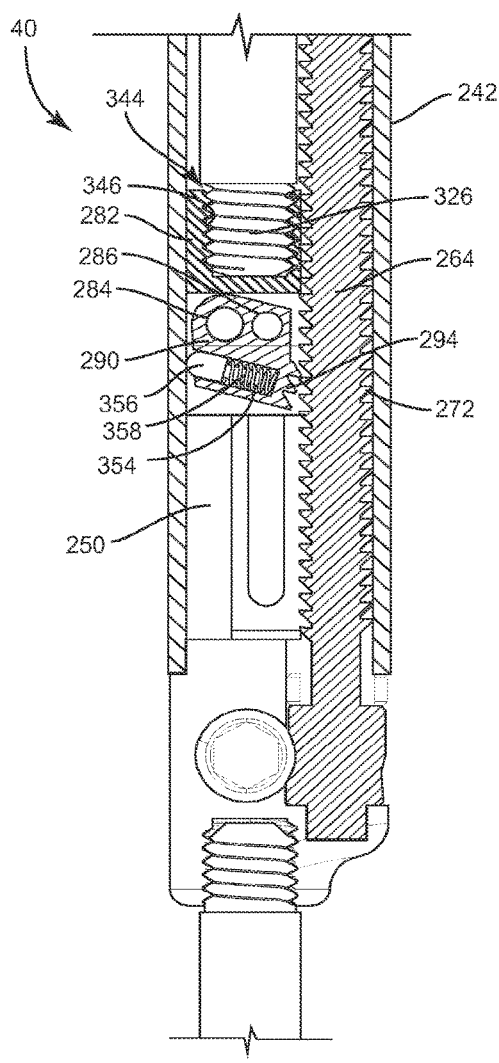
FIG. 28 is a cross sectional break away view of the system shown in FIG. 16.
Figure 29:
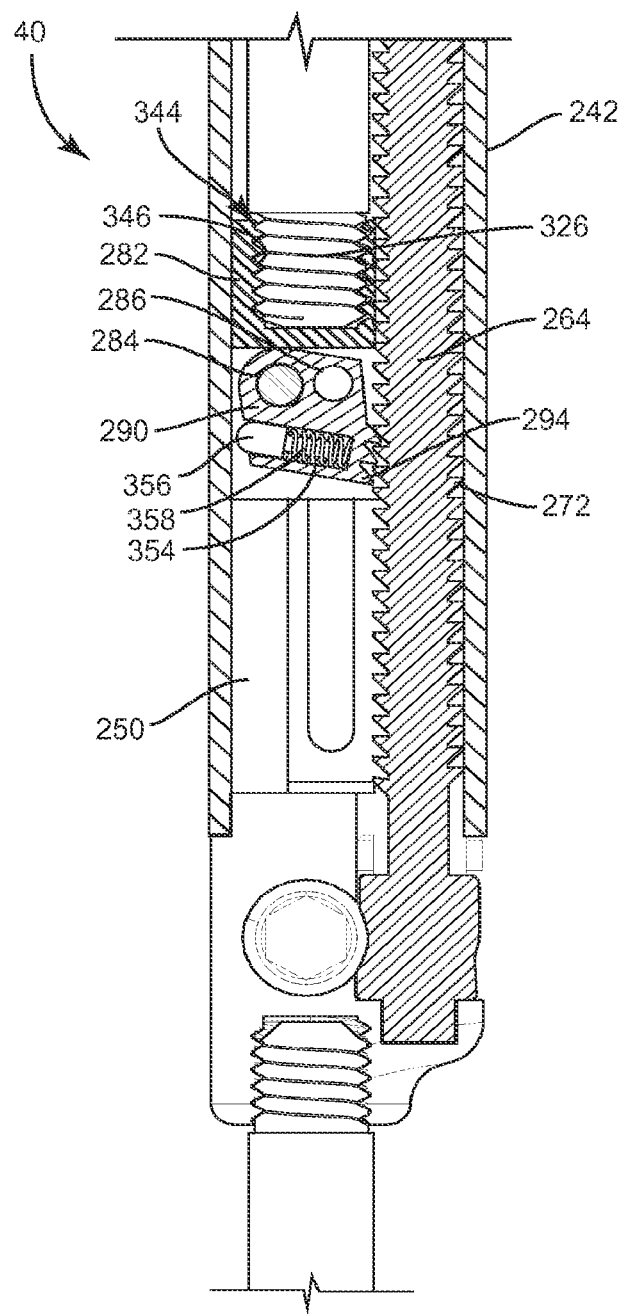
FIG. 29 is a cross sectional break away view of the system shown in FIG. 16.

Carriage 282 is advanced in the direction shown by arrow B' in FIG. 26 and teeth 294 slide over thread form 272, according to the expansion force, such as, for example, an amount of growth between the anatomical portions connected to spinal correction apparatus 40. Upon reaching an equilibrium with the expansion force, teeth 294 are disposed in a mesh engagement with thread form 272, as facilitated by the bias of pawl 290 with thread form 272. This configuration prevents contraction and/or axial movement of rod 320 relative to sleeve 242 in a direction opposite to the first axial direction and permits further expansion and/or advancement of rod 320 relative to sleeve 242, in the first axial direction, according to other forces applied to spinal correction apparatus 40 and/or subsequent patient growth. This configuration provides dynamic incremental movement of rod 320 relative to sleeve 242 in the direction shown by arrow B' in FIG. 26, to be used, for example, for stabilization of vertebrae and non-invasive lengthening and/or compensation for patient growth.

In one embodiment, as shown in FIGS. 30-31, the system comprising spinal correction apparatus 40, similar to the apparatus and methods described above with regard to FIGS. 16-29, includes a body, such as, for example, outer sleeve 442 that defines a longitudinal axis c. Outer sleeve 242 extends between a first end 444 and a second end 446. Sleeve 442 has an elliptical cross section configuration. Sleeve 442 includes an outer surface 448. Sleeve 442 includes an inner surface 450 that defines a cavity 452. Cavity 252 is configured for disposal of the components of spinal correction apparatus 40.

First end 444 is configured for movable disposal of a first longitudinal element, such as, for example, a rod 520. Second end 446 is configured for disposal of a second longitudinal element, such as, for example, a rod 522.

A ratchet 462 is connected to sleeve 442. Ratchet 462 is disposed within cavity 452 of sleeve 442. Ratchet 462 includes a rack 464 mounted to inner surface 450. Rack 464 includes gear teeth 472 disposed axially therealong.

Ratchet 462 includes a carriage assembly comprising a carriage 482. Carriage 482 includes a surface that defines a cavity 484 for support of a pin 498, which movably connects a pawl 490, described below, with carriage 482. Carriage 482 includes a cavity 544 that has a threaded surface 546. Cavity 544 is configured for disposal of rod 520 and threaded surface 546 engages the second end of rod 520 for fixation therewith. Pawl 490 includes gear teeth 494 configured for engagement with gear teeth 472. Pin 498 extends through cavity 484 and pawl 490 to connect pawl 490 to carriage 482. Pawl 490 is pivotable relative to carriage 482. Pawl 490 rotates relative to carriage 482 such that pawl 490 pivots about pin 498. Pawl 490 pivots about pin 498 to facilitate releasable engagement of teeth 494 with gear teeth 472.

Pawl 490 includes a transverse recess 554 configured for disposal of a plunger 556 and a spring 558. Plunger 556 and spring 558 are disposed within transverse recess 554 to facilitate biased movement of pawl 490 into engagement with gear teeth 472. Spring 558 biases plunger 556 against the wall of sleeve 442 such that pawl 490 pivots about pin 498 and gear teeth 494 are forced into a releasable mesh fixation and a fixed position with gear teeth 472.

Rod 520 extends between a first end 524 and a second threaded end 526. Rod 520 is inserted into sleeve 442 through first end 524. Second end 526 is fixed with carriage 482 in a threaded engagement. Rod 520 is disposed in a telescopic configuration within sleeve 442. Spinal correction apparatus 40 includes a second longitudinal element, such as, for example, rod 522. Rod 522 extends between a first end 528 and a second end (not shown). Rod 522 is inserted into sleeve 542 through second end 446.

In operation, spinal correction apparatus 40 is configured for non-invasive lengthening to compensate for patient growth, as shown in FIGS. 30-31. For example, during patient growth, a force, such as, for example, an expansion force, due to separation of anatomical body portions attached to spinal correction apparatus 40, is applied to rod 520 and/or rod 522 that causes dynamic incremental movement of rod 520 relative to sleeve 542 in a first axial direction, similar to that described above with regard to FIGS. 16-29.

Upon application of the expansion force to first end 524 of rod 520, carriage 482 is drawn in the first axial direction towards first end 444 such that teeth 494 advance axially in the first axial direction along gear teeth 472 such that teeth 494 slide over gear teeth 472. Pawl 490 is biased into engagement with gear teeth 472 via spring 558/plunger 556, described above. In one embodiment, the forces are applied to rod 522.

Carriage 482 is advanced in the first axial direction and teeth 294 slide over gear teeth 472, according to the expansion force, such as, for example, an amount of growth between the anatomical portions connected to spinal correction apparatus 40. Upon reaching an equilibrium with the expansion force, a mesh engagement of teeth 494 with gear teeth 472, as facilitated by the bias of pawl 490 with gear teeth 472, prevents contraction and/or axial movement of rod 520 relative to sleeve 442 in a direction opposite to the first axial direction and permits further expansion and/or advancement of rod 520 relative to sleeve 442, in the first axial direction, according to other forces applied to spinal correction apparatus 40 and/or subsequent patient growth. This configuration provides dynamic incremental movement of rod 520 relative to sleeve 542 in the first axial direction to be used, for example, for stabilization of vertebrae and non-invasive compensation for patient growth.

Figure 32:
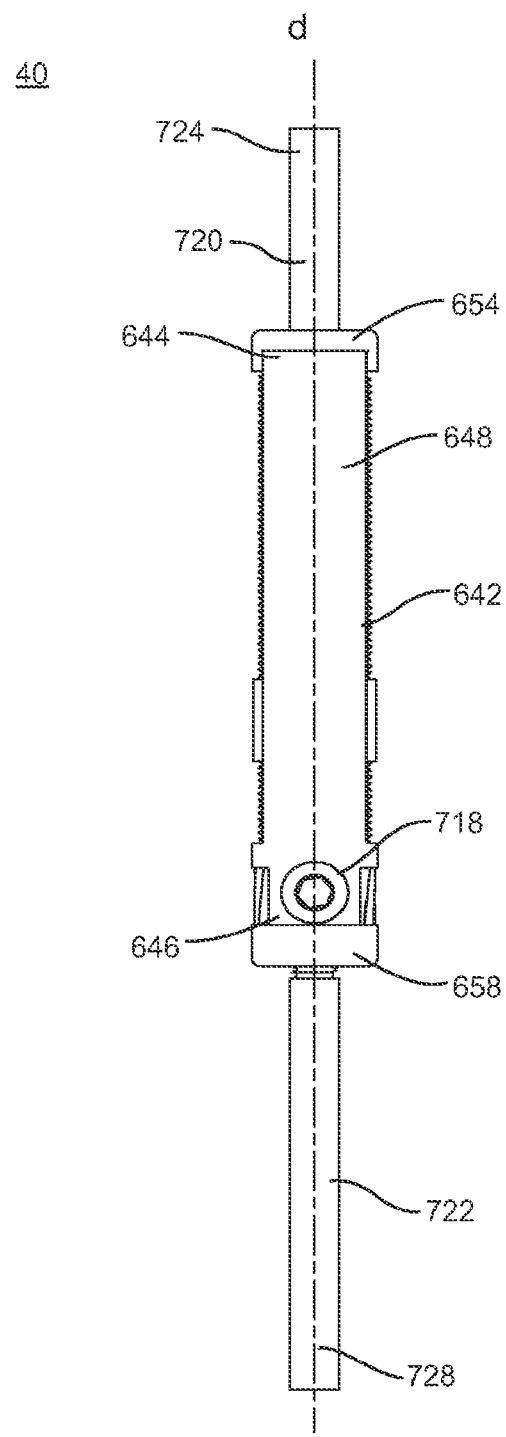
FIG. 32 is a perspective view one particular embodiment of a system including a spinal correction apparatus in accordance with the principles of the present disclosure.
Figure 33:
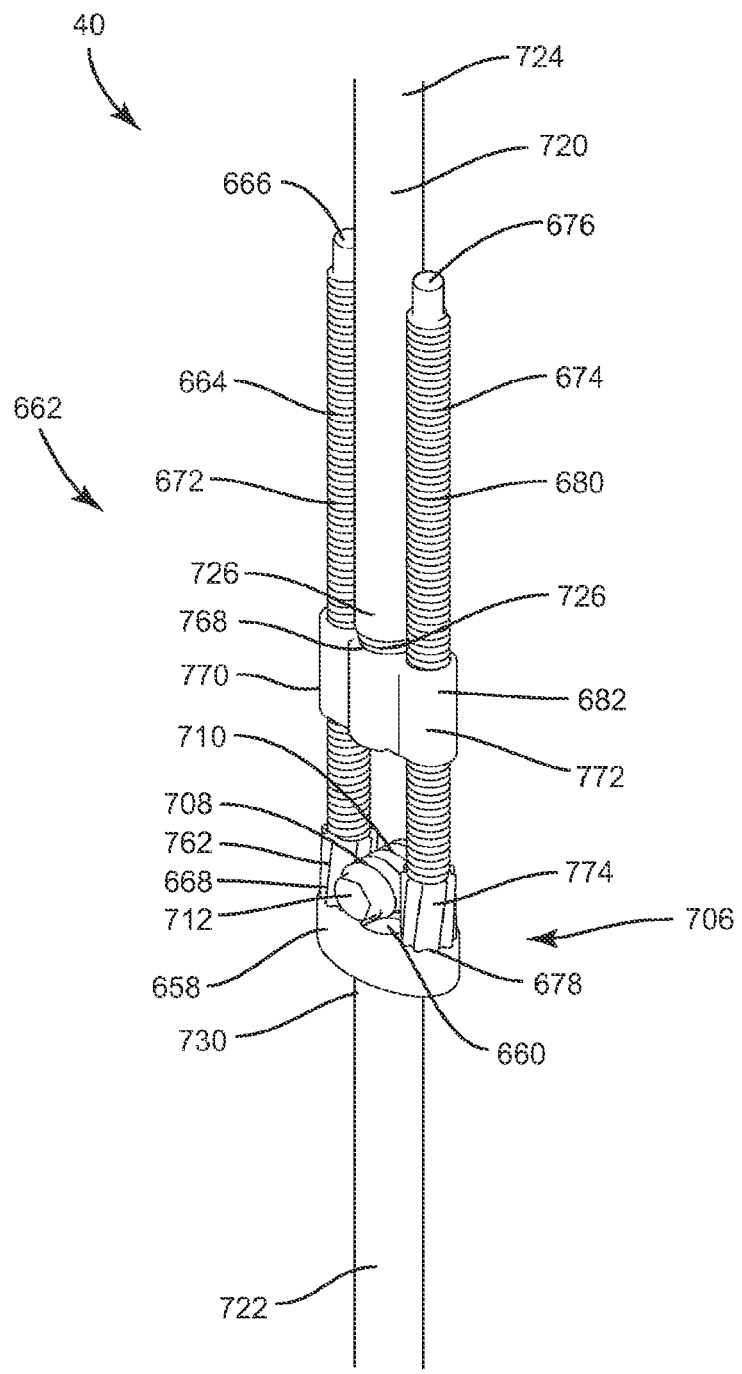
FIG. 33 is a perspective cutaway view of the system shown in FIG. 32.

In one embodiment, as shown in FIGS. 32-33, the system comprising spinal correction apparatus 40, similar to the apparatus and methods described above with regard to FIGS. 16-29, includes a body, such as, for example, outer sleeve 642 that defines a longitudinal axis d. Outer sleeve 642 extends between a first end 644 and a second end 646. Sleeve 642 includes an outer surface 648. Sleeve 642 includes an inner surface (not shown) that defines a cavity configured for disposal of the components of spinal correction apparatus 40.

An end cap 654 is disposed at first end 644 of sleeve 642 and includes an opening configured for movable disposal of a first longitudinal element, such as, for example, a rod 720, discussed below. An end cap 658 is disposed at second end 646 of sleeve 642 and includes an opening configured for disposal of a second longitudinal element, such as, for example, a rod 722, discussed below.

A ratchet 662 is connected to sleeve 642. Ratchet 662 is disposed within the cavity of sleeve 642. Ratchet 662 includes a first rack, such as, for example, a drive screw 664 and a second rack, such as, for example, a drive screw 674. Drive screws 664, 674 are mounted to the inner surface of sleeve 642 and disposed axially in a substantially parallel orientation.

Drive screw 664 extends between a first end 666 and a second end 668. Drive screw 664 includes a thread form 672 disposed axially between ends 666 and 668. Thread form 672 has a pitch that causes axial movement of a carriage assembly, discussed below. Drive screw 674 extends between a first end 676 and a second end 678. Drive screw 674 includes a thread form 680 disposed axially between ends 676 and 678. Thread form 680 has a pitch that causes axial movement of a carriage assembly, discussed below.

Ratchet 662 includes a carriage assembly comprising a carriage 682. Carriage 682 includes a first threaded cavity 770 and a second threaded cavity 772 that support drive screws 664, 674, respectively, and facilitate axial translation of drive screws 664, 674 relative thereto, as will be described. Carriage 682 includes a threaded cavity 768 configured for disposal of rod 720 and includes a threaded surface that engages a threaded portion of second end 726 for fixation therewith.

Cavities 770, 772 include thread forms configured for engagement with drive screws 664, 674. The thread forms of cavities 770, 772 movably engage thread forms 672, 680 for axial movement in at least one axial direction relative to sleeve 642 along the helical and/or spiral configuration of thread forms 672, 680.

An actuator 706 includes worm gear 708. Worm gear 708 has an outer threaded surface 710. Worm gear 708 is rotatable within an end cap 658 such that outer threaded surface 710 engages with gear teeth 762, 774 of parallel gears disposed at second end 646. End cap 658 defines a cavity that supports drive screws 664, 674. Worm gear 708 includes socket 712 having a hexagonal configuration. Socket 712 is configured for engagement with an instrument, as described below.

Actuator 706 is connected to ratchet 262 to facilitate incremental movement of rod 720 relative to sleeve 642 in at least one axial direction. Actuator 706 is rotatable in a first direction, such as, for example, a clockwise direction and a second direction, such as, for example, a counter clockwise direction to facilitate movement of rod 720 in at least one axial direction, such as, for example, a first axial direction, similar to that described above.

Rod 720 extends between a first end 724 and a second threaded end 726. Rod 720 is inserted into sleeve 642 through first end 644. Second end 726 is fixed with carriage 682 in a threaded engagement. Rod 720 is disposed in a telescopic configuration within sleeve 742. Spinal correction apparatus 40 includes a second longitudinal element, such as, for example, rod 722. Rod 722 extends between a first end 728 and a second end 730. Rod 722 is inserted into sleeve 642 through second end 646.

In operation, as shown in FIGS. 32-33, the system including spinal correction apparatus 40 includes an instrument, similar to that described above, which is manipulated to engage worm gear 708 and rotated to facilitate incremental movement of rod 720 relative to sleeve 642 in at least one axial direction. Carriage 682 is disposed adjacent second end 646.

Worm gear 708 is rotated in a clockwise direction such that threaded surface 710 engages gear teeth 762, 774 to rotate drive screws 664, 674 in a first direction. Thread forms 672, 680 engage the thread forms of cavities 770, 772 along its respective helical configuration. Carriage 682 is driven in the first axial direction towards first end 644 such that the thread forms of cavities 770, 772 advance axially in the first axial direction along the helical configuration of thread forms 672, 680.

As the drive tool is further rotated, carriage 682 is further advanced, according to the requirements of a particular application. This configuration facilitates incremental movement of rod 720 relative to sleeve 642 in the first axial direction. Movement of rod 720 relative to sleeve 642 expands the overall length of apparatus 40 to be used, for example, with a body invasive procedure for stabilization of vertebrae, initial implantation and/or to compensate for patient growth.

Spinal correction apparatus 40 can be contracted such that worm gear 708 is rotated in a counterclockwise direction. The drive tool rotates worm gear 708 such that threaded surface 710 engages gear teeth 762, 774 to rotate drive screws 664, 674 in a second direction. Thread forms 672, 680 engage the thread forms of cavities 770, 772 along its respective helical configuration. Carriage 682 is driven in a second axial direction towards second end 646 such that the thread forms of cavities 770, 772 advance axially in the second axial direction along the helical configuration of thread forms 672, 680. This configuration facilitates incremental movement of rod 720 relative to sleeve 642 in the second axial direction to compress and/or contract the overall length of spinal correction apparatus 40.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal correction apparatus comprising:
   a body extending between opposite first and second ends, the body defining a cavity;
   a ratchet disposed within the cavity, the ratchet comprising a rack and a carriage that are each disposed within the cavity, the ratchet comprising a pawl that is pivotable about a pin that extends through the carriage;
   a first longitudinal element disposed within the cavity and connected to the carriage such that the first longitudinal element extends through an opening in the first end;
   a second longitudinal element disposed within the cavity such that the second longitudinal element extends through an opening in the second end and is coaxial with the first longitudinal element, the second longitudinal element being spaced apart from the first longitudinal element, and
   an actuator disposed within a housing of the rack and configured to facilitate incremental movement of the first longitudinal element relative to the body in at least one axial direction,
   wherein an expansion force applied to the first longitudinal element causes dynamic incremental movement of the first longitudinal element relative to the body in a first axial direction, independent of the actuator.

2. An apparatus as recited in claim 1, wherein the first longitudinal element is disposed in a telescopic configuration with the body.

3. An apparatus as recited in claim 1, wherein the actuator comprises a cam that is rotatable within a transverse channel of the housing in at least one direction to facilitate axial movement of the first longitudinal element.

4. An apparatus as recited in claim 1, wherein the actuator comprises a cam that is rotatable within a transverse channel of the housing in a first direction and a second direction to facilitate movement of the first longitudinal element in the first axial direction.

5. An apparatus as recited in claim 1, wherein the actuator defines a socket configured for engagement with an instrument.

6. An apparatus as recited in claim 1, wherein the first longitudinal element is connected with the ratchet and configured for movement in a first axial direction only.

7. An apparatus as recited in claim 1, wherein the first longitudinal element comprises an outer surface that is threaded with a threaded cavity of the carriage.

8. An apparatus as recited in claim 1, wherein the body comprises a ridge extending from an inner surface of the body, the rack comprising a flange having a notch, the ridge being disposed in the notch.

9. An apparatus as recited in claim 8, wherein the flange comprises a passageway, the first longitudinal element extending through the passageway.

10. An apparatus as recited in claim 1, wherein the rack comprises a first end defining a flange, an opposite second end defining the housing and an intermediate portion between the first and second ends of the rack, the intermediate portion comprising gear teeth, the first end of the rack and the second end of the rack each being monolithically formed with the intermediate portion.

11. An apparatus as recited in claim 10, wherein the flange comprises a circular passageway, the first longitudinal element extending through the passageway.

12. An apparatus as recited in claim 1, wherein the actuator is disposed within a transverse channel of the housing, the actuator being rotatable relative to the body and the housing to facilitate movement of the first longitudinal element relative to the body and the ratchet.

13. An apparatus as recited in claim 1, wherein the pawl is engageable with gear teeth of the rack, the apparatus further comprising a second rack defined by an inner surface of the body, the second rack including gear teeth, the ratchet comprising a second pawl that is pivotable about the pin and configured for engagement with the gear teeth of the second rack.

14. A spinal correction apparatus comprising:
a body extending between opposite first and second ends, the body defining a cavity;
a ratchet disposed within the body, the ratchet comprising a rack and a carriage that are each disposed within the cavity, the ratchet comprising a pawl that is pivotable about a pin that extends through the carriage;
a first longitudinal element disposed within the cavity and having a threaded outer surface connected to a threaded inner surface of the carriage such that the first longitudinal element extends through an opening in the first end, the pawl being engageable with the rack to facilitate axial movement of the first longitudinal element;
a second longitudinal element disposed within the cavity such that the second longitudinal element extends through an opening in the second end and is coaxial with the first longitudinal element, the second longitudinal element being spaced apart from the first longitudinal element; and
an actuator disposed within a housing of the rack, the actuator being rotatable relative to the body and the housing to facilitate movement of the first longitudinal element relative to the body.

15. A spinal correction apparatus comprising:
a body extending between opposite first and second ends, an inner surface of the body defining a cavity and a first rack;
a ratchet disposed within the cavity, the ratchet comprising a second rack and a carriage that are each disposed within the cavity, the ratchet comprising a first pawl and a second pawl that are each pivotable about a pin, the pin extending through the pawls and the carriage, the first pawl being configured for engagement with gear teeth of the first rack, the second pawl being configured for engagement with gear teeth of the second rack;
a first longitudinal element disposed within the cavity and connected to the carriage such that the first longitudinal element extends through an opening in the first end, the pawls being engageable with the gear teeth to facilitate axial movement of the first longitudinal element;
a second longitudinal element disposed within the cavity such that the second longitudinal element extends through an opening in the second end and is coaxial with the first longitudinal element; and
an actuator disposed within a housing of the second rack, the actuator being rotatable relative to the body and the housing to facilitate movement of the first longitudinal element relative to the body.

16. An apparatus as recited in claim 15, wherein the body comprises a rack ridge extending from an inner surface of the body, the second rack comprising a flange having a notch, the ridge being disposed in the notch, the flange comprising a passageway, the first longitudinal element extending through the passageway.

17. An apparatus as recited in claim 15, wherein the body comprises a ridge extending from an inner surface of the body, the carriage comprising a body having a notch, the ridge being disposed in the notch.

18. An apparatus as recited in claim 15, wherein the actuator comprises a cam positioned in a transverse channel of the housing, the housing being disposed within the cavity.

* * * * *